(12) United States Patent
Mahmoud et al.

(10) Patent No.: US 10,570,155 B2
(45) Date of Patent: Feb. 25, 2020

(54) IMIDAZOOXAZOLE DERIVATIVE HAVING ANTITUMOR EFFECT, AND PHARMACEUTICAL COMPOSITION INCLUDING SAME

(71) Applicant: KOREA INSTITUTE OF SCIENCE AND TECHNOLOGY, Seoul (KR)

(72) Inventors: Gamal El-din Mahmoud, Dokki-giza (EG); Hong Seok Choi, Gwangju (KR); Kyung Ho Yoo, Seoul (KR); Dong Keun Han, Seoul (KR); Chang Hyun Oh, Seoul (KR); Abdel-Maksoud Mohammed, Dokki-giza (EG); I. El-Gamal Mohammed, Sharjah (AE)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 16/315,263

(22) PCT Filed: Jul. 3, 2017

(86) PCT No.: PCT/KR2017/007021
§ 371 (c)(1),
(2) Date: Feb. 13, 2019

(87) PCT Pub. No.: WO2018/008920
PCT Pub. Date: Jan. 11, 2018

(65) Prior Publication Data
US 2019/0211032 A1 Jul. 11, 2019

(30) Foreign Application Priority Data
Jul. 5, 2016 (KR) .................. 10-2016-0085062

(51) Int. Cl.
C07D 513/04 (2006.01)
C07D 498/04 (2006.01)
A61P 35/00 (2006.01)

(52) U.S. Cl.
CPC ............ C07D 513/04 (2013.01); A61P 35/00 (2018.01); C07D 498/04 (2013.01)

(58) Field of Classification Search
CPC ........................... C07D 513/04; C07D 498/04
See application file for complete search history.

(56) References Cited

U.S. PATENT DOCUMENTS

| 2008/0161341 A1 | 7/2008 | Calderwood et al. |
| 2009/0312310 A1 | 12/2009 | Kawato et al. |
| 2010/0183600 A1 | 7/2010 | Lapierre et al. |
| 2015/0203498 A1 | 7/2015 | Leclercq et al. |

FOREIGN PATENT DOCUMENTS

| KR | 10-2009-0090383 A | 8/2009 |
| KR | 10-2011-0100241 A | 9/2011 |
| WO | WO 2004/110990 A2 | 12/2004 |
| WO | WO-2007123892 A2 * | 11/2007 ........... C07D 513/04 |
| WO | WO 2016/042172 A1 | 3/2016 |

OTHER PUBLICATIONS

J-H Park et al., Bull. Korean Chem. Soc. (2010) (Year: 2010).*
M.S. Abdel-Maksoud et al., 95 European Journal of Medicinal Chemistry (2015) (Year: 2015).*
M.S. Abdel-Maksoud et al., 27 Bioorganic & Medicinal Chemistry, 2041-2051 (2019) (Year: 2019).*
Abdel-Maksoud et al., "Design, synthesis, in vitro antiproliferative evaluation, and kinase inhibitory effects of a new series of imidazo[2,1-b]thiazole derivatives", European Journal of Medicinal Chemistry, vol. 95, 2015, pp. 453-463.
International Search Report issued in PCT/KR2017/007021 (PCT/ISA/210), dated Sep. 19, 2017.
Office Action for Korean Patent Application No. 10-2016-0085062, dated Jul. 10, 2018.
Park et al., "Synthesis of New 6-(4-Fluorophenyl)-5-(2-substituted pyrimidin-4-yl)imidazo[2,1-b]thiazole Derivatives and their Antiproliferative Activity against Melanoma Cell Line", Bulletin of the Korean Chemistry Society, vol. 31, No. 10, pp. 2854-2860.
Written Opinion of the International Searching Authority issued in PCT/KR2017/007021 (PCT/ISA/237), dated Sep. 19, 2017.
Abdel-Maksoud et al., "Design, synthesis, in vitro antiproliferative evaluation, and kinase inhibitory effects of a new series of imidazo[2,1-b]thiazole derivatives," European Journal of Medicinal Chemistry (2015), vol. 95, pp. 453-463.
Davies et al., "Mutations of the BRAF gene in human cancer," Nature (Jun. 27, 2002), vol. 417, pp. 949-954.
Hoeflich et al., "Oncogenic BRAF is Required for Tumor Growth and Maintenance in Melanoma Models," Cancer Res. (2006), vol. 66, No. 2, pp. 999-1006.
Marais, R., and C. J. Marshall, "Control of the ERK MAP kinase cascasde by Ras and Raf.," Cancer Surv. (1996), vol. 27, pp. 101-125, Abstract.
Rajagopalan et al., "RAF/RAS oncogenes and mismatch-repair status," Nature (Aug. 29, 2002), vol. 418, p. 934.
Sharma et al., Mutatnt $^{V599E}$B-Raf Regulates Growth and Vascular Development of Malignant Melanoma Tumors, Cancer Res. (2005), vol. 65, No. 6, pp. 2412-2421.
Tuveson et al., "BRAF as a potential therapeutic target in melanoma and other malignancies," Cancer Cell (Aug. 2003), vol. 4, pp. 95-98.
Wellbrock et al., "$^{V599E}$B-RAF is an Oncogene in Melanocytes," Cancer Research (Apr. 1, 2004), vol. 64, pp. 2338-2342.

(Continued)

Primary Examiner — Alexander R Pagano
(74) Attorney, Agent, or Firm — Birch, Stewart, Kolasch & Birch, LLP

(57) ABSTRACT

Provided is a pharmaceutical composition for preventing and treating tumors, the pharmaceutical composition including an imidazooxazole derivative compound, a solvate, a stereoisomer, or a pharmaceutically acceptable salt thereof as an active ingredient. The pharmaceutical composition is administered to an entity which has developed a tumor or is in danger of developing a tumor, and thus tumors can be prevented or treated.

10 Claims, 1 Drawing Sheet

(56) References Cited

OTHER PUBLICATIONS

Xing, M., "BRAF mutation in thyroid cancer," Endocrine-Related Cancer (2005), vol. 12, pp. 245-262.
Extended European Search Report issued Oct. 29, 2019, in European Patent Application No. 17824476.0.

* cited by examiner

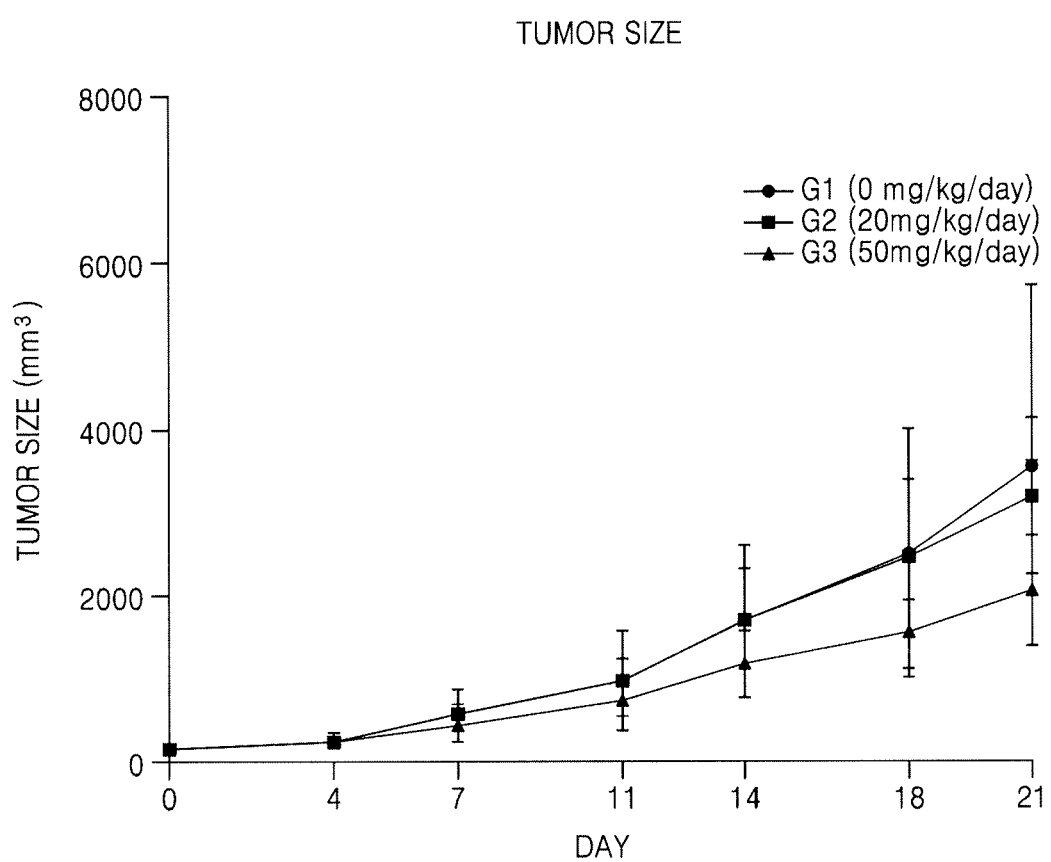

IMIDAZOOXAZOLE DERIVATIVE HAVING ANTITUMOR EFFECT, AND PHARMACEUTICAL COMPOSITION INCLUDING SAME

CROSS REFERENCE TO RELATED APPLICATIONS

This application is the National Phase of PCT International Application No. PCT/KR2017/007021, filed on Jul. 3, 2017, which claims priority under 35 U.S.C. 119(a) to Patent Application No. 10-2016-0085062, filed in the Republic of Korea on Jul. 5, 2016, all of which are hereby expressly incorporated by reference into the present application.

TECHNICAL FIELD

The present disclosure relates to an imidazooxazole derivative or a pharmaceutically acceptable salt thereof, a method of preparing the same, and a pharmaceutical composition for preventing or treating tumors including the same as an active ingredient.

BACKGROUND ART

The mitogen-activated protein kinase (MAPK) signaling pathway (EGFR>Ras>Raf>Mek>Erk) is a signaling pathway involved in cell proliferation, which has been considered to be important in tumorigenesis in many studies since it was discovered in 1990.

There are three RAF kinase enzymes in humans: A-RAF, B-RAF, and C-RAF (Marais and Marshall Cancer Surv. 27: 101-125, 1996). Since mutations of B-RAF were found at a high frequency in human cancer, RAF proteins were recognized as a critical initiator and promoter of malignancy (Davies, H. et al. Nature 417: 949-954 (2002)).

B-RAF mutations have been identified in approximately 7% of cancers, including 50% to 70% of melanomas, 35% of ovarian cancers, 50% of thyroid cancers, and 10% of colorectal cancers (Tuveson, et al., Cancer Cell. 4:95-98 (2003); and Xing, Endocrine-Related Cancer: 12:245-262 (2005)). Approximately 90% of the mutations occur as a point mutation (V600E) in which a valine residue is changed to a glutamate residue in the kinase domain. This V600E is an important target for the development of cancer therapeutics. A V600E mutation confers an approximately 500-fold increase in kinase activity, resulting in hyperactivation of MEK and ERK and abnormal growth of tumor cells. Until now, about 40 B-RAF mutations have been found (mainly at the activation segment and the glycine-rich G-loop of the kinase catalytic domain). However, the occurrence of mutations other than V600E is fairly infrequent. In corectal cancer, about 10% of B-RAF mutations occur at the G-loop of the kinase domain (Rajagopalan et al., Nature 2002 418, 934).

Recent studies have found that knockdown of mutant B-RAF by siRNA in human melanoma cells inhibits both MEK and ERK, causing growth arrest of tumor cells and ultimately promoting apoptosis (Sharma, et al., Canfer Res. 65:2412-2421 (2005); and Wellbrock et al., Cancer Res. 64:2338-2342 (2004)). In addition, experimental results from short-hairpin RNA xenograft models targeting mutant B-RAF have shown that tumor regression resulting from B-RAF suppression is reversibly regulated (Hoeflich et al., Cancer Res. 66:999-1006 (2006). Taken together, in-vivo B-RAF signaling is strongly associated with tumorigenicity, confirming B-RAF as an important target for cancer therapeutics.

DESCRIPTION OF EMBODIMENTS

Technical Problem

An aspect provides an imidazooxazole derivative compound or a solvate, stereoisomer, or pharmaceutically acceptable salt thereof.

Another aspect provides a pharmaceutical composition for preventing and treating tumors, the pharmaceutical composition including the imidazooxazole derivative compound or the solvate, stereoisomer, or pharmaceutically acceptable salt thereof as an active ingredient.

Still another aspect provides a method of preventing or treating tumors, the method including administering the pharmaceutical composition to a subject having or at risk of developing a tumor.

Solution to Problem

An aspect provides a compound represented by the following Chemical Formula S or a solvate, stereoisomer, or pharmaceutically acceptable salt thereof, wherein:

[Chemical Formula S]

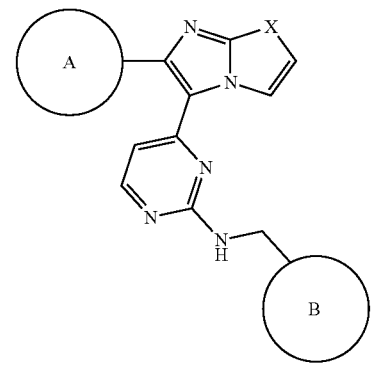

A is

wherein,
when X is O, $R^1$ is hydrogen, halogen, $C_1$-$C_4$ alkoxy, hydroxyl, or a combination thereof, and
when X is S, $R^1$ is hydrogen, Cl, Br, I, $C_1$-$C_4$ alkoxy, hydroxyl, or a combination thereof; and
B is

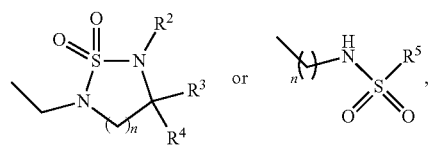

wherein, n=1 or 2, $R^2$, $R^3$, and $R^4$ are each independently hydrogen, tert-butyloxycarbonyl, or $C_1$-$C_4$ linear or branched alkyl, $C_5$-$C_{12}$ aryl, $C_5$-$C_{12}$ heteroaryl, or $C_5$-$C_{12}$ heterocycloalkyl unsubstituted or substituted with one or more substituents, and $R^5$ is M or M-Y, wherein M and Y are each independently $C_5$-$C_{12}$ aryl, $C_5$-$C_{12}$ heteroaryl, $C_5$-$C_{12}$ aryl, $C_1$-$C_4$ alkyl, $C_5$-$C_{12}$ heteroaryl, $C_1$-$C_4$ alkyl, $C_5$-$C_{12}$ cycloalkyl, or $C_5$-$C_{12}$ heterocycloalkyl unsubstituted or substituted with one or more substituents, wherein the one or more substituents may be selected from the group consisting of halogen, $C_1$-$C_4$ linear or branched alkyl, $C_1$-$C_4$ alkoxy, trifluoromethyl, hydroxyl, amine, $C_1$-$C_4$ alkylamine, nitro, amide, $C_1$-$C_4$ alkylamide, urea, and acetyl.

In one embodiment, when X is O, $R^1$ is hydrogen, fluoro, methoxy, hydroxyl, or a combination thereof, $R^2$, $R^3$, and $R^4$ are each independently hydrogen, tert-butyloxycarbonyl, ethyl, methyl, or benzyl, and $R^5$ is phenyl unsubstituted or substituted with one or more substituents, wherein the substituent may be selected from the group consisting of methyl, ethyl, fluoro, trifluoromethyl, hydroxyl, methoxy, nitro, amide, urea, and acetyl.

The 'halogen' may be F, Cl, Br, or I.

The 'alkoxy' may be methoxy, ethoxy, n-propoxy, iso-propoxy, n-butoxy, isobutoxy, or t-butoxy.

The 'alkyl' refers to a linear or branched aliphatic hydrocarbon group having a particular number of carbon atoms, and may be methyl, ethyl, n-propyl, isopropyl, butyl, isobutyl, or t-butyl.

The 'aryl' may be phenyl, naphthyl, anthracenyl, indanyl, or biphenyl.

The 'heteroaryl' or 'heterocycloalkyl' may be azetidinyl, acridinyl, benzodioxolyl, benzodioxanyl, benzofuranyl, carbazolyl, cinnolinyl, dioxolanyl, pyridyl, pteridinyl, purinyl, quinazolinyl, quinoxalinyl, quinolinyl, isoquinolinyl, tetrazolyl, imidazolyl, tetrahydroisoquinolinyl, pyrrolyl, piperonyl, pyrazinyl, pyrimidinyl, pyridazinyl, pyrazolyl, oxazolyl, oxazolinyl, triazolyl, indanyl, isoxazolyl, isoxazolidinyl, decahydroisoquinolyl, benzimidazolyl, indazolyl, phenylpiperidinyl, furyl, tetrahydrofuryl, tetrahydropyranyl, piperazinyl, homopiperazinyl, piperidyl, piperidopiperidyl, morpholinyl, thiomorpholinyl, piperidinyl, 2-oxopiperazinyl, 2-oxopiperidinyl, pyrrolidinyl, 2-oxopyrrolidinyl, or oxazolidinyl.

The 'cycloalkyl' may be selected from cyclopropyl, cyclobutyl, cyclopentyl, cyclohexyl, cyclooctyl, cycloheptyl, perhydronaphthyl, adamantyl, cross-linked cyclic groups, and spirobicyclic groups.

In another embodiment, the compound may be represented by any one of the following Chemical Formulae I to IV:

[Chemical Formula I]

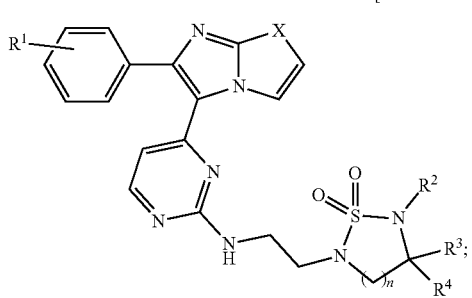

[Chemical Formula II]

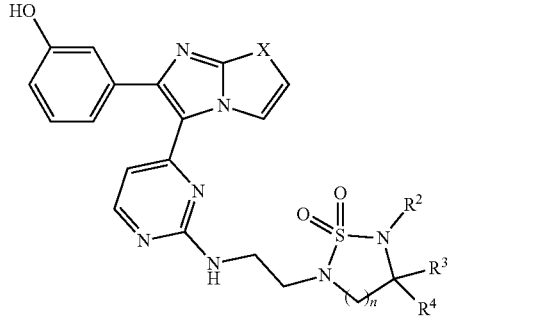

[Chemical Formula III]

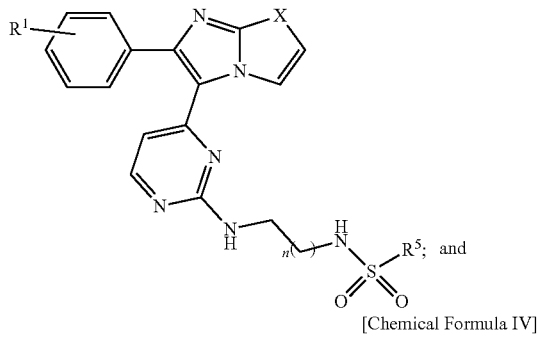

[Chemical Formula IV]

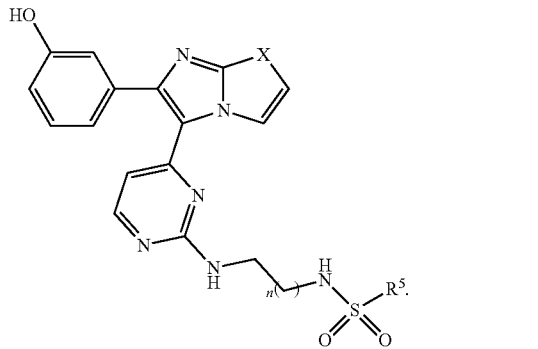

In the above Chemical Formulae, X, n, $R^1$, $R^2$, $R^3$, $R^4$, and $R^5$ are the same as mentioned above.

In still another embodiment, the compound represented by Chemical Formula S may be selected from the group consisting of 2-(2-((4-(6-(4-fluorophenyl)imidazo[2,1-b]oxazol-5-yl)pyrimidin-2-yl)amino)ethyl)-5-methyl-1,2,5-thiadiazolidine 1,1-dioxide (1I);

2-ethyl-5-(2-((4-(6-(4-fluorophenyl)imidazo[2,1-b]oxazol-5-yl)pyrimidin-2-yl)amino)ethyl)-1,2,5-thiadiazolidine 1,1-dioxide (2I);

2-benzyl-5-(2-((4-(6-(4-fluorophenyl)imidazo[2,1-b]oxazol-5-yl)pyrimidin-2-yl)amino)ethyl)-1,2,5-thiadiazolidine 1,1-dioxide (3I);

2-(2-((4-(6-(3-methoxyphenyl)imidazo[2,1-b]oxazol-5-yl)pyrimidin-2-yl)amino)ethyl)-5-methyl-1,2,5-thiadiazolidine 1,1-dioxide (4I);

2-ethyl-5-(2-((4-(6-(3-methoxyphenyl)imidazo[2,1-b]oxazol-5-yl)pyrimidin-2-yl)amino)ethyl)-1,2,5-thiadiazolidine 1,1-dioxide (5I);

2-benzyl-5-(2-((4-(6-(3-methoxyphenyl)imidazo[2,1-b]oxazol-5-yl)pyrimidin-2-yl)amino)ethyl)-1,2,5-thiadiazolidine 1,1-dioxide (6I);

2-(2-((4-(6-(3-methoxyphenyl)imidazo[2,1-b]oxazol-5-yl)pyrimidin-2-yl)amino)ethyl)-1,2,5-thiadiazolidine 1,1-dioxide (7I);

2-(2-((4-(6-(3-methoxyphenyl)imidazo[2,1-b]oxazol-5-yl)pyrimidin-2-yl)amino)ethyl)-4,4-dimethyl-1,2,5-thiadiazolidine 1,1-dioxide (8I);

2-(2-((4-(6-(3-methoxyphenyl)imidazo[2,1-b]oxazol-5-yl)pyrimidin-2-yl)amino)ethyl)-6-methyl-1,2,6-thiadiazinane 1,1-dioxide (9I);

2-(2-((4-(6-(3-methoxyphenyl)imidazo[2,1-b]oxazol-5-yl)pyrimidin-2-yl)amino)ethyl)-1,2,6-thiadiazinane 1,1-dioxide (10I);

2-(2-((4-(6-(3-hydroxylphenyl)imidazo[2,1-b]oxazol-5-yl)pyrimidin-2-yl)amino)ethyl)-5-methyl-1,2,5-thiadiazolidine 1,1-dioxide (1II);

2-ethyl-5-(2-((4-(6-(3-hydroxylphenyl)imidazo[2,1-b]oxazol-5-yl)pyrimidin-2-yl)amino)ethyl)-1,2,5-thiadiazolidine 1,1-dioxide (2II);

2-benzyl-5-(2-((4-(6-(3-hydroxylphenyl)imidazo[2,1-b]oxazol-5-yl)pyrimidin-2-yl)amino)ethyl)-1,2,5-thiadiazolidine 1,1-dioxide (3II);

2-(2-((4-(6-(3-hydroxylphenyl)imidazo[2,1-b]oxazol-5-yl)pyrimidin-2-yl)amino)ethyl)-1,2,5-thiadiazolidine 1,1-dioxide (4II);

2-(2-((4-(6-(3-hydroxylphenyl)imidazo[2,1-b]oxazol-5-yl)pyrimidin-2-yl)amino)ethyl)-4,4-dimethyl-1,2,5-thiadiazolidine 1,1-dioxide (5II);

2-(2-((4-(6-(3-hydroxylphenyl)imidazo[2,1-b]oxazol-5-yl)pyrimidin-2-yl)amino)ethyl)-6-methyl-1,2,6-thiadiazinane 1,1-dioxide (6II);

tert-butyl-6-(2-((4-(6-(3-hydroxylphenyl)imidazo[2,1-b]oxazol-5-yl)pyrimidin-2-yl)amino)ethyl)-1,2,6-thiadiazinane-2-carboxylate 1,1-dioxide (7II);

2-(2-((4-(6-(3-hydroxylphenyl)imidazo[2,1-b]oxazol-5-yl)pyrimidin-2-yl) amino)ethyl)-1,2,6-thiadiazinane 1,1-dioxide (8II);

4-fluoro-N-(2-((4-(6-phenylimidazo[2,1-b]thiazol-5-yl)pyrimidin-2-yl)amino)ethyl)benzenesulfonamide (1III);

4-methoxy-N-(2-((4-(6-phenylimidazo[2,1-b]thiazol-5-yl)pyrimidin-2-yl)amino)ethyl)benzenesulfonamide (2III);

4-methyl-N-(2-((4-(6-phenylimidazo[2,1-b]thiazol-5-yl)pyrimidin-2-yl)amino)ethyl)benzenesulfonamide (3III);

N-(2-((4-(6-(4-fluorophenyl)imidazo[2,1-b]oxazol-5-yl)pyrimidin-2-yl)amino)ethyl)benzenesulfonamide (4IV);

3-fluoro-N-(2-((4-(6-(4-fluorophenyl)imidazo[2,1-b]oxazol-5-yl)pyrimidin-2-yl)amino)ethyl)benzenesulfonamide (5IV);

4-fluoro-N-(2-((4-(6-(4-fluorophenyl)imidazo[2,1-b]oxazol-5-yl)pyrimidin-2-yl)amino)ethyl)benzenesulfonamide (6IV);

N-(2-((4-(6-(4-fluorophenyl)imidazo[2,1-b]oxazol-5-yl)pyrimidin-2-yl)amino)ethyl)-4-iodobenzenesulfonamide (7IV);

N-(2-((4-(6-(4-fluorophenyl)imidazo[2,1-b]oxazol-5-yl)pyrimidin-2-yl)amino)ethyl)-4-methoxybenzenesulfonamide (8IV);

N-(2-((4-(6-(4-fluorophenyl)imidazo[2,1-b]oxazol-5-yl)pyrimidin-2-yl)amino)ethyl)-4-methyl benzenesulfonamide (9IV);

N-(2-((4-(6-(4-fluorophenyl)imidazo[2,1-b]oxazol-5-yl)pyrimidin-2-yl)amino)ethyl)-4-(trifluoromethyl)benzenesulfonamide (10IV);

N-(2-((4-(6-(4-fluorophenyl)imidazo[2,1-b]oxazol-5-yl)pyrimidin-2-yl)amino)ethyl)-3,4-dimethoxybenzenesulfonamide (11IV);

N-(2-((4-(6-(4-fluorophenyl)imidazo[2,1-b]oxazol-5-yl)pyrimidin-2-yl)amino)ethyl)-3,4-dimethylbenzenesulfonamide (12IV);

N-(2-((4-(6-(4-fluorophenyl)imidazo[2,1-b]oxazol-5-yl)pyrimidin-2-yl)amino)ethyl)naphthalene-2-sulfonamide (13IV);

N-(2-((4-(6-(3-methoxyphenyl)imidazo[2,1-b]thiazol-5-yl)pyrimidin-2-yl)amino)ethyl)benzenesulfonamide (4III);

4-fluoro-N-(2-((4-(6-(3-methoxyphenyl)imidazo[2,1-b]thiazol-5-yl)pyrimidin-2-yl)amino)ethyl)benzenesulfonamide (5III);

4-methoxy-N-(2-((4-(6-(3-methoxyphenyl)imidazo[2,1-b]thiazol-5-yl)pyrimidin-2-yl)amino)ethyl)benzenesulfonamide (6III);

N-(2-((4-(6-(3-methoxyphenyl)imidazo[2,1-b]thiazol-5-yl)pyrimidin-2-yl)amino)ethyl)-4-methylbenzenesulfonamide (7III);

N-(2-((4-(6-(3-methoxyphenyl)imidazo[2,1-b]thiazol-5-yl)pyrimidin-2-yl)amino)ethyl)-4-(trifluoromethyl)benzenesulfonamide (8III);

3-fluoro-N-(2-((4-(6-(3-methoxyphenyl)imidazo[2,1-b]thiazol-5-yl)pyrimidin-2-yl)amino)ethyl)benzenesulfonamide (9III);

N-(2-((4-(6-(3-methoxyphenyl)imidazo[2,1-b]thiazol-5-yl)pyrimidin-2-yl)amino)ethyl)naphthalene-2-sulfonamide (10III);

4-fluoro-N-(2-((4-(6-(4-methoxyphenyl)imidazo[2,1-b]thiazol-5-yl)pyrimidin-2-yl)amino)ethyl)benzenesulfonamide (11III);

4-methoxy-N-(2-((4-(6-(4-methoxyphenyl)imidazo[2,1-b]thiazol-5-yl)pyrimidin-2-yl)amino)ethyl)benzenesulfonamide (12III);

N-(2-((4-(6-(4-methoxyphenyl)imidazo[2,1-b]thiazol-5-yl)pyrimidin-2-yl)amino)ethyl)-4-methylbenzenesulfonamide (13III);

N-(2-((4-(6-(4-methoxyphenyl)imidazo[2,1-b]thiazol-5-yl)pyrimidin-2-yl)amino)ethyl)naphthalene-2-sulfonamide (14III);

4-fluoro-N-(3-((4-(6-phenylimidazo[2,1-b]thiazol-5-yl)pyrimidin-2-yl)amino)propyl)benzenesulfonamide (15III);

4-methoxy-N-(3-((4-(6-phenylimidazo[2,1-b]thiazol-5-yl)pyrimidin-2-yl)amino)propyl)benzenesulfonamide (16III);

4-methyl-N-(3-((4-(6-phenylimidazo[2,1-b]thiazol-5-yl)pyrimidin-2-yl)amino)propyl)benzenesulfonamide (17III);

N-(3-((4-(6-(4-fluorophenyl)imidazo[2,1-b]oxazol-5-yl)pyrimidin-2-yl)amino)propyl)benzenesulfonamide (28IV);

4-fluoro-N-(3-((4-(6-(4-fluorophenyl)imidazo[2,1-b]oxazol-5-yl)pyrimidin-2-yl)amino)propyl)benzenesulfonamide (29IV);

N-(3-((4-(6-(4-fluorophenyl)imidazo[2,1-b]oxazol-5-yl)pyrimidin-2-yl)amino)propyl)-4-iodobenzenesulfonamide (30IV);

N-(3-((4-(6-(4-fluorophenyl)imidazo[2,1-b]oxazol-5-yl)pyrimidin-2-yl)amino)propyl)-4-methoxybenzenesulfonamide (31IV);

N-(3-((4-(6-(4-fluorophenyl)imidazo[2,1-b]oxazol-5-yl)pyrimidin-2-yl)amino)propyl)-4-methylbenzenesulfonamide (32IV);

N-(3-((4-(6-(4-fluorophenyl)imidazo[2,1-b]oxazol-5-yl)pyrimidin-2-yl)amino)propyl)-4-(trifluoromethyl)benzenesulfonamide (33IV);

3-fluoro-N-(3-((4-(6-(4-fluorophenyl)imidazo[2,1-b]oxazol-5-yl)pyrimidin-2-yl)amino)propyl)benzenesulfonamide (34IV);

N-(3-((4-(6-(4-fluorophenyl)imidazo[2,1-b]oxazol-5-yl)pyrimidin-2-yl)amino)propyl)-3,4-dimethoxybenzenesulfonamide (35IV);
N-(3-((4-(6-(4-fluorophenyl)imidazo[2,1-b]oxazol-5-yl)pyrimidin-2-yl)amino)propyl)-3,4-dimethylbenzenesulfonamide (36IV);
N-(3-((4-(6-(4-fluorophenyl)imidazo[2,1-b]oxazol-5-yl)pyrimidin-2-yl)amino)propyl)naphthalene-2-sulfonamide (37IV);
N-(3-((4-(6-(3-methoxyphenyl)imidazo[2,1-b]thiazol-5-yl)pyrimidin-2-yl)amino)propyl)benzenesulfonamide (18III);
3-fluoro-N-(3-((4-(6-(3-methoxyphenyl)imidazo[2,1-b]thiazol-5-yl)pyrimidin-2-yl)amino)propyl)benzenesulfonamide (19III);
4-fluoro-N-(3-((4-(6-(3-methoxyphenyl)imidazo[2,1-b]thiazol-5-yl)pyrimidin-2-yl)amino)propyl)benzenesulfonamide (20III);
4-methoxy-N-(3-((4-(6-(3-methoxyphenyl)imidazo[2,1-b]thiazol-5-yl)pyrimidin-2-yl)amino)propyl)benzenesulfonamide (21III);
N-(3-((4-(6-(3-methoxyphenyl)imidazo[2,1-b]thiazol-5-yl)pyrimidin-2-yl)amino)propyl)-4-methylbenzenesulfonamide (22III);
N-(3-((4-(6-(3-methoxyphenyl)imidazo[2,1-b]thiazol-5-yl)pyrimidin-2-yl)amino)propyl)naphthalene-2-sulfonamide (23III);
4-hydroxyl-N-(2-((4-(6-phenylimidazo[2,1-b]thiazol-5-yl)pyrimidin-2-yl)amino)ethyl)benzenesulfonamide (24III);
N-(2-((4-(6-(4-fluorophenyl)imidazo[2,1-b]oxazol-5-yl)pyrimidin-2-yl)amino)ethyl)-4-hydroxylbenzenesulfonamide (45IV);
4-fluoro-N-(2-((4-(6-(3-hydroxylphenyl)imidazo[2,1-b]thiazol-5-yl)pyrimidin-2-yl)amino)ethyl)benzenesulfonamide (25III);
4-hydroxyl-N-(2-((4-(6-(3-hydroxylphenyl)imidazo[2,1-b]thiazol-5-yl)pyrimidin-2-yl)amino)ethyl)benzenesulfonamide (26III);
N-(2-((4-(6-(3-hydroxylphenyl)imidazo[2,1-b]thiazol-5-yl)pyrimidin-2-yl)amino)ethyl)-4-methylbenzenesulfonamide (27III);
4-hydroxyl-N-(2-((4-(6-(4-hydroxylphenyl)imidazo[2,1-b]thiazol-5-yl)pyrimidin-2-yl)amino)ethyl)benzenesulfonamide (28III);
N-(2-((4-(6-(4-hydroxylphenyl)imidazo[2,1-b]thiazol-5-yl)pyrimidin-2-yl)amino)ethylbenzenesulfonamide (29III);
N-(3-((4-(6-(4-fluorophenyl)imidazo[2,1-b]oxazol-5-yl)pyrimidin-2-yl)amino)propyl)-4-hydroxylbenzenesulfonamide (51IV);
N-(3-((4-(6-(3-hydroxylphenyl)imidazo[2,1-b]thiazol-5-yl)pyrimidin-2-yl)amino)propyl)benzenesulfonamide (30III); and
4-fluoro-N-(3-((4-(6-(3-hydroxylphenyl)imidazo[2,1-b]thiazol-5-yl)pyrimidin-2-yl)amino)propyl)benzenesulfonamide (31III).

An aspect provides a method of preparing the compound represented by Chemical Formula S or the solvate, stereoisomer, or pharmaceutically acceptable salt thereof, the method including:
cyclizing a compound of Chemical Formula 1 and a compound of Chemical Formula 2 to prepare a compound of Chemical Formula 3;
reacting the compound of Chemical Formula 3 with 4-chloro-2-(methylthio)pyrimidine to prepare a compound of Chemical Formula 4;
oxidizing the compound of Chemical Formula 4 to prepare a compound of Chemical Formula 5; and
reacting the compound of Chemical Formula 5 with an N-aminoethylcyclic sulfonamide derivative or an N-(2-aminoethyl)benzenesulfonamide derivative in the presence of a base to prepare the compound of Chemical Formula S.

Specifically, the preparation method may be represented by the following Reaction Scheme 1:

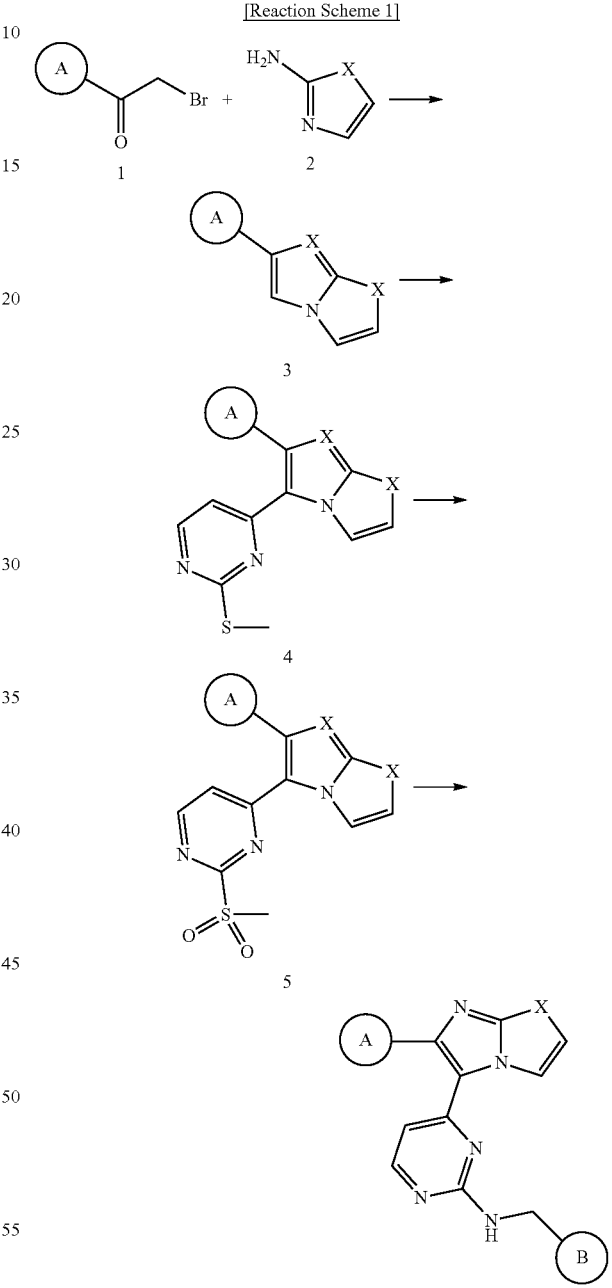

In Reaction Scheme 1, A, B, and X are the same as defined above.

In a specific embodiment, preparation of the compound of Chemical Formula 4 by reacting the compound of Chemical Formula 3 with 4-chloro-2-(methylthio)pyrimidine may be performed under Heck reaction conditions in the presence of Pd(OAc)$_2$ as a catalyst. Each procedure may further include purification as needed. In the procedure 4, the base may be diisopropylethylamine (DIPEA).

Another aspect provides a pharmaceutical composition for preventing and treating tumors, the pharmaceutical composition including the compound or the solvate, stereoisomer, or pharmaceutically acceptable salt thereof as an active ingredient.

Still another aspect provides use of a composition including the compound or the solvate, stereoisomer, or pharmaceutically acceptable salt thereof in the preparation of the pharmaceutical composition.

The 'pharmaceutically acceptable salt' is any organic or inorganic acid addition salt of the compound of Chemical Formula S which is at such a concentration that is relatively nontoxic to a patient and has a harmless effective action, and adverse effects from the salt do not counteract benefits of the compound of Chemical Formula S. These salts may use an inorganic acid or an organic acid as a free acid. As an inorganic acid, hydrochloric acid, bromic acid, nitric acid, sulfuric acid, perchloric acid, phosphoric acid, etc. may be used. As an organic acid, citric acid, acetic acid, lactic acid, maleic acid, fumaric acid, gluconic acid, methanesulfonic acid, glycolic acid, succinic acid, tartaric acid, galacturonic acid, embonic acid, glutamic acid, aspartic acid, oxalic acid, (D) or (L) malic acid, maleic acid, methanesulfonic acid, ethanesulfonic acid, 4-toluenesulfonic acid, salicilic acid, citric acid, benzoic acid, malonic acid, etc. may be used. These salts may include alkali metal salts (sodium salt, potassium salt, etc.) and alkali earth metal salts (calcium salt, magnesium salt, etc.). For example, the acid addition salt may include acetate, aspartate, benzoate, besylate, bicarbonate/carbonate, bisulfate/sulfate, borate, camcilate, citrate, edisylate, ethylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, methylate, methylsulfate, naphthalate, 2-naphthylate, nicotinate, nitrate, orotate, oxalate, palmitate, pamoate, phosphate/hydrogen phosphate/dihydrogen phosphate, saccharate, stearate, succinate, tartrate, tosylate, trifluoroacetate, aluminum, arginine, benzathine, calcium, choline, diethylamine, diolamine, glycine, lysine, magnesium, meglumine, olamine, potassium, sodium, tromethamine, zinc salt, etc. Among them, hydrochloride or trifluoroacetate may be used.

In a specific embodiment, the compound or the solvate, stereoisomer, or pharmaceutically acceptable salt thereof may inhibit protein kinase to inhibit proliferation of tumor cells. The protein kinase is involved in proliferation of tumor cells, and may be one or more selected from the group consisting of V600E Rapidly Accelerated Fibrosarcoma (RAF), B-RAF, C-RAF, Mitogen-activated protein kinase 14 (MAPK14), Fms-like tyrosine kinase 3 (FLT3), and Glycogen synthase kinase 3 beta (GSK3β).

In another specific embodiment, the tumors may be lung cancer, liver cancer, esophageal cancer, stomach cancer, colorectal cancer, small intestine cancer, pancreatic cancer, melanoma, breast cancer, oral cancer, bone cancer, brain tumor, thyroid cancer, parathyroid cancer, renal cancer, cervical cancer, sarcoma, prostate cancer, urethral cancer, bladder cancer, testicular cancer, leukemia, multiple myeloma, myelodysplastic syndrome, hematological malignancy such as or glioblastoma, lymphoma such as Hodgkin's disease and non-Hodgkin lymphoma, Behcet's disease, skin cancer, psoriasis, and fibroadenoma.

An aspect provides a method of preventing or treating tumors, the method including administering the compound or the solvate, stereoisomer, or pharmaceutically acceptable salt thereof to a subject having or at risk of developing a tumor.

The subject may be a mammal, and the mammal may be a human. An administration dose of the compound of the present disclosure which is effective for a human body may vary depending on a patient' age, body weight, sex, administration mode, health conditions, and severity of disease.

The administration may be performed by various formulations for oral administration or parenteral administration such as intravenous, intraperitoneal, intradermal, subcutaneous, epithelial, or intramuscular administration. The formulations may be prepared using a commonly used diluent or excipient such as a filler, an extender, a binder, a wetting agent, a disintegrant, a surfactant, etc.

Solid formulations for oral administration may include tablets, pills, powders, granules, capsules, troches, etc., and such a solid formulation is prepared by mixing one or more compounds of the present disclosure with at least one excipient, for example, starches, calcium carbonate, sucrose, lactose, gelatin, etc. Also, lubricants such as magnesium stearate and talc may be used in addition to simple excipients. Liquid formulations for oral administration may include suspensions, solutions for internal use, emulsions, syrups, etc. Various excipients, for example, wetting agents, sweetening agents, fragrances, preservatives, etc. may be included in addition to water and liquid paraffin which are simple diluents commonly employed.

Formulations for parenteral administration may include sterilized aqueous solutions, non-aqueous solutions, suspensions, emulsions, lyophilized formulations, suppositories, etc. Examples of non-aqueous solutions or suspensions may include propylene glycol, polyethylene glycol, vegetable oil such as olive oil, an injectable ester such as ethyl oleate, etc. Examples of suppository bases may include Witepsol, macrogol, Tween 61, cacao butter, laurin fat, glycerol, gelatin, etc.

BRIEF DESCRIPTION OF DRAWINGS

FIG. 1 shows tumor size according to the number of days after transplantation, which represents anti-cancer effects after administration of compound 2II to A375P cell line xenograft models (G1 indicates an excipient control group, G2 indicates a group administered with 20 mg/kg/day of a test material, and G3 indicates a group administered with 50 mg/kg/day of a test material).

MODE OF DISCLOSURE

Hereinafter, the present disclosure will be described in more details with reference to Examples. However, these Examples are for illustrative purposes only, and the scope of the present disclosure is not intended to be limited thereto.

Preparation Method 1

Compounds of Chemical Formulae I to IV were prepared according to the following procedures, as shown in Reaction Schemes 2 and 3.

A method of synthesize an imidazooxazole compound is the same as in the following Reaction Scheme 2, and for synthesis of the compounds of Chemical Formulae I to IV, it is important to synthesize a compound 5 which is a main intermediate.

Reaction Scheme 2

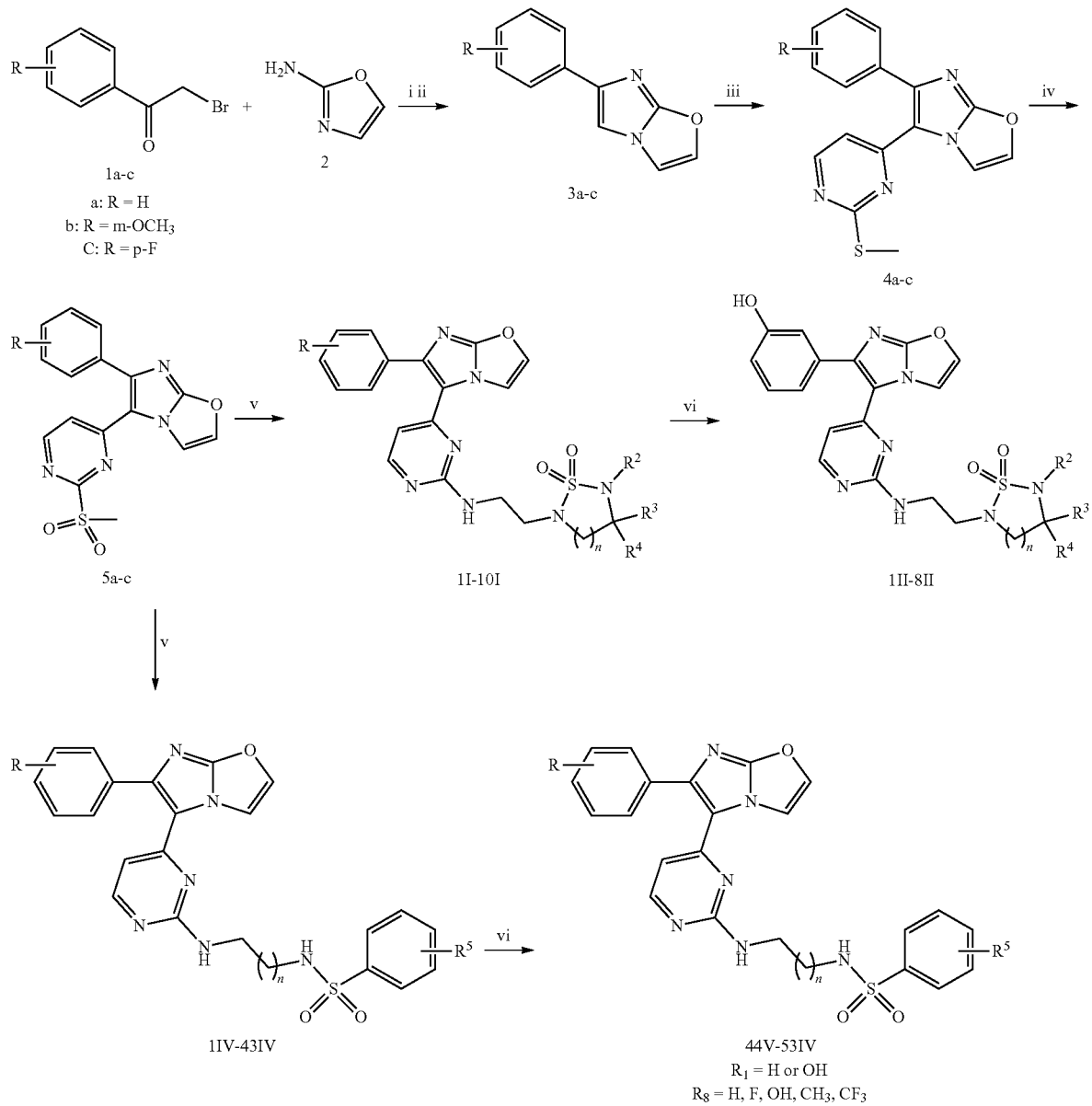

Reagents and Conditions: i) CH₃CN, THF, room temperature, 24 hours; ii) TiCl₄, toluene, reflux; iii) 4-chloro-2-(methylthio)pyrimidine, palladium acetate, triphenylphosphine, cesium carbonate, DMF, 80° C., 16 hours; iv) oxone, methanol, H₂O; v) N-(2-aminoethyl)benzene sulfonamide or N-aminoethyl cyclicsulfonamide, DIPEA, DMSO, 80° C.; vi) BBr₃, dichloromethane.

Cyclization was carried out by reacting 2-aminooxazole (2) with α-bromo-4-fluoroacetophenone in ethanol under reflux for 16 hours, and crystallization was carried out using ammonia to synthesize a compound 3. The compound 3 thus synthesized was reacted with 4-chloro-2-(methylthio) pyrimidine in the presence of Pd(OAc)₂ catalyst under Heck reaction conditions at 80° C. for 36 hours. After the reaction was completed, column chromatography was used to obtain a methylthiopyrimidinyl compound 4. The compound 4 thus synthesized was oxidized using oxone at room temperature overnight, and purified by a column to synthesize a compound 5 which is a key intermediate. Under diisopropylethylamine, N-aminoethyl cyclic sulfonamide or N-(2-aminoethyl)benzenesulfonamide was dissolved in a DMF solvent, and stirred at 80° C. for 5 hours to 10 hours to obtain compounds I, II, and IV. Among these compounds, a methoxy compound was dissolved in methylene chloride, and cooled at −78° C. Then, BBr₃ was slowly added dropwise, and stirred for 30 minutes. The temperature was raised to room temperature, and demethylation was carried out for 12 hours to synthesize a target compound having a hydroxyl group.

Preparation Method 2

A method of synthesizing an imidazothiazole compound is the same as in the following Reaction Scheme 3, and the method was carried out in the same manner as in Reaction Scheme 2, except that 2-aminothiazole (2) was used.

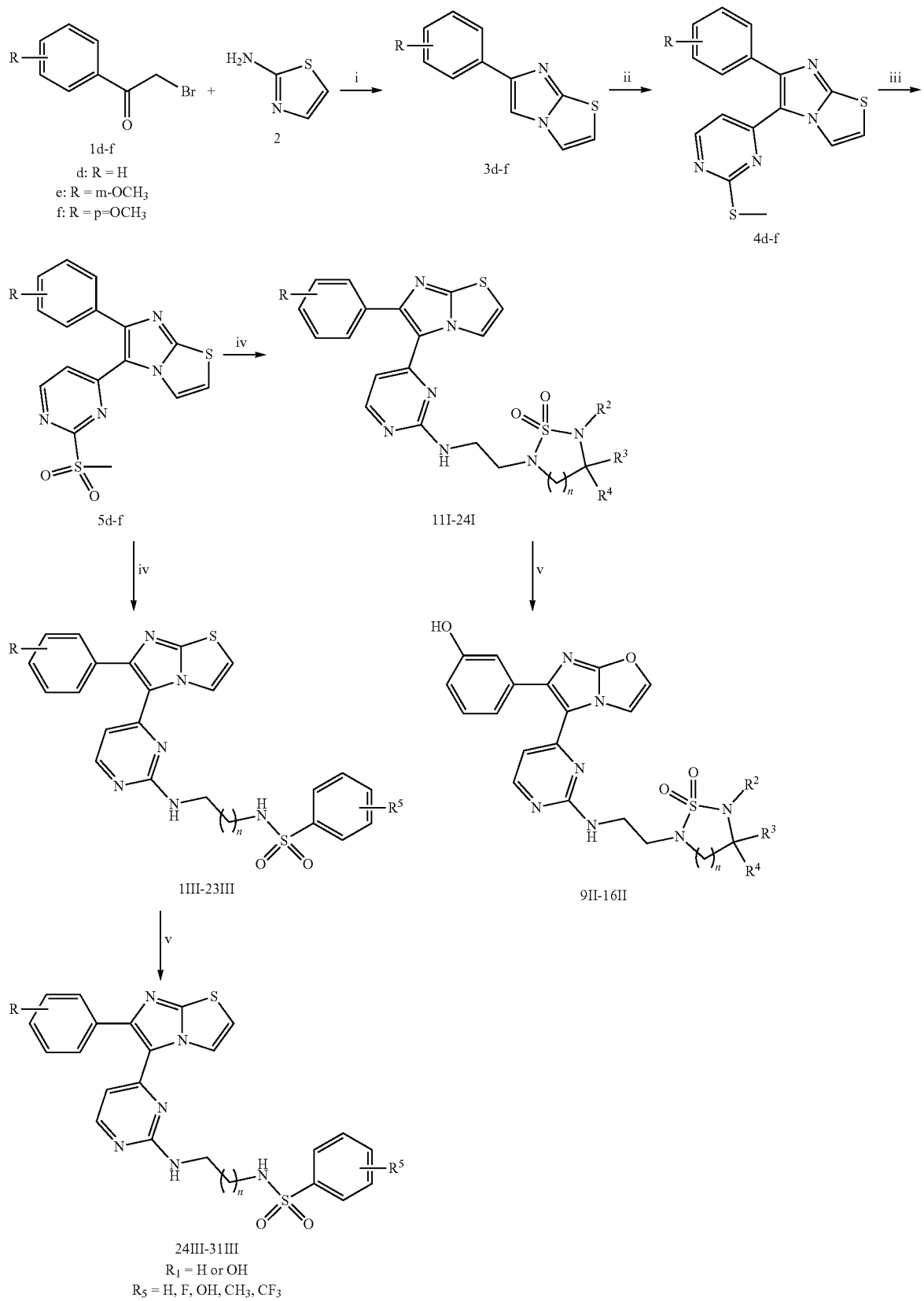

Reagents and Conditions: i) ethanol, reflux; overnight, ii) 4-chloro-2-(methylthio)pyrimidine, palladium acetate, triphenylphosphine, cesium carbonate, DMF, 80° C., 16 hours; iii) oxone, methanol, H$_2$O; iv) N-(2-aminoethyl)benzenesulfonamide or N-aminoethyl cyclic sulfonamide, DIPEA, DMSO, 80° C.; v) BBr$_3$, dichloromethane.

The compound of each reaction scheme is shown in the following Example.

Example 1. 6-Phenylimidazo[2,1-b]oxazole (3a in Reaction Scheme 2)

To acetonitrile (120 mL), 2-aminooxazole (2 in Reaction Scheme 2, 4.7 g, 47.4 mmol) and α-bromo-4-acetophenone (10.8 g, 49.9 mmol) were added, and stirred at room temperature for 48 hours. Completion of the reaction was confirmed by TLC, followed by filtration. A produced solid was added to toluene (100 mL). 20 mL of titanium chloride (1 M dichloromethane solution) was slowly added to the suspension at 0° C. This reaction solution was refluxed and stirred for 20 hours, and concentrated to one half of its initial volume. A saturated sodium carbonate solution was added thereto, and extracted with ethyl acetate. An organic layer was dried over anhydrous Na$_2$SO$_4$, followed by filtration. The resulting product was distilled under reduced pressure and concentrated to obtain a target compound of 6-phenylimidazo[2,1-b]oxazole (3a) in a crystal state.

White solid (5.1 g, 56%). mp 143-144° C.; IR (KBr) [cm$^{-1}$]: 3139, 3120, 1955, 1884, 1602. $^1$H-NMR (DMSO-d$_6$, 300 MHz) δ 8.63 (d, 1H, J=7.17 Hz), 8.29 (t, 1H, J=5.71 Hz), 7.77 (t, 3H, J=6.7 Hz), 7.49-7.36 (m, 3H). $^{13}$CNMR (DMSO-d$_6$, 75 MHz) δ 158.1, 154.4, 134.9, 132.6, 127.7, 125.7, 121.9, 119.6, 111.5, 104.2.

Example 2. 5-(2-(Methylthio)pyrimidin-4-yl)-6-phenylimidazo[2,1-b]oxazole (4a in Reaction Scheme 2)

6-Phenylimidazo[2,1-b]oxazole (compound 3a, 8.26 g, 37.8 mmol), 4-chloro-2-(methylthio)pyrimidine (9.09 g, 56.6 mmol), cesium carbonate (18.44 g, 56.6 mmol), palladium acetate (1.71 g, 7.6 mmol), and triphenylphosphine (3.96 g, 15.1 mmol) were added to DMF (80 mL) and stirred at 80° C. for 36 hours. Completion of the reaction was confirmed by TLC, and the reaction solution was cooled to room temperature. EtOAc (200 mL) and distilled water (250 mL) were added to separate layers. An aqueous layer was extracted with EtOAc (100 mL) three times, and discarded. An organic layer was washed with saline (100 mL), and dried over anhydrous Na$_2$SO$_4$, followed by filtration. The resulting product was distilled under reduced pressure and concentrated, and then purified by flash column chromatography to obtain 4.37 g of a target compound of 6-phenyl-5-(2-(methylthio)pyrimidin-4-yl)imidazo[2,1-b]oxazole (4a) in a crystal state.

White solid (19%), mp. 143-144° C.; IR (KBr) [cm$^{-1}$]: 3054, 6103, 1538, 1685; $^1$H-NMR (CDCl$_3$, 300 MHz) δ 8.62 (dd, 1H, J=4.53, J=0.7), 8.23 (dd, 1H, J=5.4, J=0.7), 7.65-7.62 (m, 2H), 7.47-7.45 (m, 3H), 6.97 (dd, 1H, J=4.53, J=0.66), 6.89 (dd, 1H, J=4.77, J=0.66), 2.64 (s, 3H); $^{13}$C NMR (CDCl$_3$, 75 MHz) δ 172.4, 156.2, 156.2, 152.7, 151.1, 134.6, 129.2, 128.9, 128.8, 122.2, 120.1, 112.7, 112.0, 14.2.

Example 3. 5-(2-(Methylsulfonyl)pyrimidin-4-yl)-6-phenylimidazo[2,1-b]oxazole (5a in Reaction Scheme 2)

6-phenyl-5-(2-(methylthio)pyrimidin-4-yl)imidazo[2,1-b]oxazole (Compound 4a, 3.0 g, 8.8 mmol) was added to MeOH (300 mL). While stirring at room temperature, oxone (14.76 g, 97.0 mmol) in distilled water (60 mL) was added thereto, followed by stirring for 16 hours. Completion of the reaction was confirmed by TLC, and the organic solvent was removed by distillation under reduced pressure. DCM (60 mL) was added to an aqueous layer to separate layers. An aqueous layer was extracted with DCM (30 mL) three times, and the aqueous layer was discarded. An organic layer was washed with saline (50 mL) and distilled water (50 mL), and dried over anhydrous Na$_2$SO$_4$, followed by filtration. The resulting product was distilled under reduced pressure and concentrated, and then purified by flash column chromatography to obtain 2.69 g of a target compound of 6-phenyl-5-(2-(methylsulfonyl)pyrimidin-4-yl)imidazo[2,1-b]oxazole (5a) in a crystal state.

White solid (85%); $^1$H-NMR (CDCl$_3$, 300 MHz) δ 8.89 (d, 1H, J=4.30), 8.56 (d, 1H, J=5.40), 7.71 (d, 2H, J=2.50), 7.64-7.45 (m, 3H), 7.42 (d, 1H, J=5.20), 7.17 (d, 1H, J=4.40), 3.45 (s, 3H); $^{13}$C NMR (CDCl$_3$, 75 MHz) δ 165.7, 157.5, 156.8, 153.3, 134.1, 133.3, 130.0, 129.5, 129.1, 129.0, 128.3, 119.5, 117.5, 113.8, 39.3.

Example 4. 6-(4-Fluorophenyl)-5-(2-(methylsulfonyl)pyrimidin-4-yl)imidazo[2,1-b]oxazole (5c in Reaction Scheme 2)

This compound was synthesized in the same manner as in the synthesis of compound 5a.

Yellow solid (85%); mp. 115-116° C. $^1$H-NMR (CDCl$_3$, 300 MHz) δ 8.90 (d, 1H, J=4.5 Hz), 8.53 (d, 1H, J=5.6 Hz) 7.63 (q, 2H, J=4.7 Hz), 7.33 (d, 1H, J=5.6 Hz), 7.22 (t, 2H, J=8.6 Hz), 7.10 (d, 1H, J=4.5 Hz), 3.37 (s, 3H); $^{13}$CNMR (CDCl$_3$, 75 MHz) δ 171.1, 165.7, 157.3, 157.0, 154.2, 151.7, 131.0, 130.9, 129.9, 123.1, 119.4, 117.4, 116.4, 116.1, 114.2, 39.2.

Example 5. 5-(2-(Methylsulfonyl)pyrimidin-4-yl)-6-phenylimidazo[2,1-b]thiazole (5d in Reaction Scheme 3)

This compound was synthesized in the same manner as in the synthesis of compound 5a.

White solid (95%); mp. 176-177° C. IR (KBr) [cm$^1$]: 3137, 3110, 2931, 1979, 1902, 1797, 1444, 1373; $^1$H-NMR (CDCl$_3$, 300 MHz) δ 8.99 (d, 1H, J=4.41), 8.58 (d, 1H, J=5.40), 7.73 (d, 2H, J=2.46), 7.66-7.47 (m, 3H), 7.45 (d, 1H, J=5.22), 7.17 (d, 1H, J=4.41), 3.47 (s, 3H); $^{13}$CNMR (CDCl$_3$, 75 MHz) δ 165.7, 157.5, 156.8, 153.3, 134.1, 133.3, 130.0, 129.5, 129.1, 129.0, 128.3, 119.5, 117.5, 113.8, 39.3; LC-MS: Predicted value calculated with respect to C$_{16}$H$_{12}$N$_4$O$_2$S$_2$ m/z: 356. Measured value: 357 (M+1)$^+$.

Example 6. 2-Methyl-1,2,5-thiadiazolidine 1,1-dioxide (6a)

N-methylethylendiamine (1.5 g, 20.8 mmol) and sulfuric diimide (2.0 g, 20.8 mmol) were added to a pyridine solvent (20 mL), and refluxed, stirred, and heated for 3 hours. After the reaction was completed, toluene (5 mL) was added to the reactant, followed by concentration and extraction with ethyl acetate. An organic solvent layer was dried over MgSO$_4$ and filtered to remove the solvent. A residue was purified by column chromatography (EtOAc) to obtain a compound 6a.

White solid (52.3%). Mp 80 to 82° C.; $^1$H-NMR (CDCl$_3$, 300 MHz) δ7.27 (s, 1H), 3.53-3.19 (m, 2H), 3.42-3.37 (m, 2H), 2.75 (s, 1H); $^{13}$C NMR (CDCl$_3$, 75 MHz) δ 32.67, 39.64, 46.94; LC-MS: Predicted value calculated with respect to $C_3H_8N_2O_2S$ m/z: 136. Measured value: 137 $(M+1)^+$.

Example 7. Benzyl(2-(5-methyl-1,1-dioxido-1,2,5-thiadiazolidin-2-yl)ethyl) carbamate (7a)

Under nitrogen atmosphere, the compound 6a (0.856 g, 6.26 mmol) was dissolved in 5 mL of anhydrous DMSO, and 60% NaH (0.282 g, 11.8 mmol) was slowly added dropwise at 0° C. The temperature was raised to room temperature, and then the solution was stirred for 1 hour. 2-(((benzyloxy)carbonyl)amino)ethyl methane sulfonate (1.5 g, 5.83 mmol) was slowly added dropwise at 0° C., and then stirred at room temperature for 5 hours. After the reaction was completed, extraction was performed with ethyl acetate, and an organic solvent layer was dried over MgSO4. Filtration was performed to remove the solvent, and a residue was purified by column chromatography (EtOAc) to obtain a compound 7a (0.82 g).

Sticky oil (42.9%). $^1$H-NMR (CDCl$_3$, 300 MHz) δ7.36-7.30 (m, 5H), 5.19 (bs, 1H), 5.10 (s, 2H), 3.46 (q, 2H, J=5.9 Hz), 3.36-3.26 (m, 4H), 3.20 (t, 2H, J=6.0 Hz). LC-MS: Predicted value calculated with respect to $C_{13}H_{19}N_3O_4S$ m/z: 313. Measured value: 314 $(M+1)^+$.

Example 8. Synthesis of 2-(2-aminoethyl)-5-methyl-1,2,5-thiadiazolidine 1,1-dioxide (8a)

The compound 7a (0.82 g, 2.5 mmol) was dissolved in 10 mL of methanol, and then 10% Pd/C (0.40 g) was added thereto. Hydrogenation was performed for 2 hours, filtration was performed, and the solvent was removed by distillation under reduced pressure. A product was used in the next reaction without purification (yield: 91%).

Example 9. N-(2-aminoethyl)-4-fluorobenzenesulfonamide (11b)

White solid (72%); mp. 108 to 109; IR (KBr) cm$^{-1}$: 3582, 3350, 3299, 3107, 3068, 1903, 1317, 838; $^1$H-NMR (CDCl$_3$, 300 MHz) δ7.84-7.79 (m, 2H), 7.11 (t, 2H, J=6 Hz), 2.89 (t, 2H, J=6 Hz), 2.71 (t, 2H, J=6 Hz). $^{13}$C NMR (CDCl$_3$, 75 MHz) δ166.7, 136.0, 129.7 (J=33), 116.3 (J=90), 45.2, 40.9. LC-MS: Predicted value calculated with respect to $C_8H_{11}FN_2O_2S$ m/z: 218 Measured value: 219 $(M+1)^+$.

Example 10. 2-(2-((4-(6-(4-Fluorophenyl)imidazo[2,1-b]oxazol-5-yl)pyrimidin-2-yl)amino)ethyl)-5-methyl-1,2,5-thiadiazolidine 1,1-dioxide (1I)

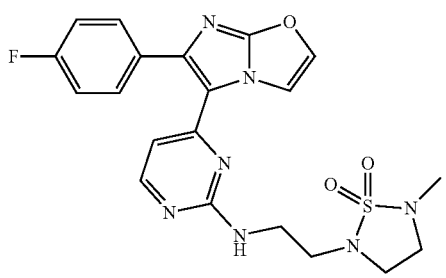 [SMILES: CN1CCN(CCNc2nccc(-c3c(-c4ccc(F)cc4)nc4occn34)n2)S1(=O)=O]

Light yellow solid; to DMSO (5 mL), 6-(4-fluorophenyl)-5-(2-(methylsulfonyl)pyrimidin-4-yl)imidazo[2,1-b]thiazole (compound 5c, 0.19 g, 0.50 mmol), 2-(2-aminoethyl)-5-methyl-1,2,5-thiadiazolidine 1,1-dioxide (compound 8a, 0.27 g, 1.24 mmol), and DIPEA (0.29 mL, 1.70 mmol) were added and stirred at 80° C. for 8 hours. This mixture was cooled to room temperature, and distilled water (10 mL) and EtOAc (10 mL) were added to separate layers. An aqueous layer was extracted with EtOAc (10 mL) twice and discarded. An organic layer was washed with saline (10 mL), and dried over anhydrous Na$_2$SO$_4$, followed by filtration. A product was concentrated under reduced pressure, and purified by recrystallization using DCM (1 mL) and hexane (3 mL) to obtain 0.18 g of a target compound 1I in a crystal form.

(72%); $^1$H-NMR (CDCl$_3$, 300 MHz) δ 8.52 (d, 1H, J=4.5 Hz), 8.08 (s, 1H), 7.61 (q, 2H, J=4.6 Hz), 7.13 (t, 2H, J=8.5 Hz), 6.91 (d, 1H, J=4.5 Hz), 6.55 (d, 1H, J=5.5 Hz), 5.81 (bs, 1H), 3.78 (q, 2H, J=6.1 Hz), 3.43-3.30 (m, 6H), 2.79 (s, 3H);

Example 11. 2-(2-((4-(6-(3-Methoxyphenyl)imidazo[2,1-b]oxazol-5-yl)pyrimidin-2-yl)amino)ethyl)-5-methyl-1,2,5-thiadiazolidine 1,1-dioxide (4I)

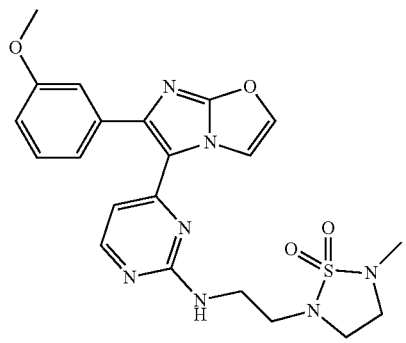 [SMILES: COc1cccc(-c2nc3occn3c2-c2ccnc(NCCN3CCN(C)S3(=O)=O)n2)c1]

This compound was synthesized in the same manner as in the synthesis of compound 1I.

White solid (50.5%); mp 144-145° C.; $^1$HNMR (CDCl$_3$, 300 MHz) 8.58 (d, 1H, J=4.5 Hz), 8.06 (d, 1H, J=5.3 Hz), 7.33 (t, 1H, J=7.8 Hz), 7.23-7.19 (m, 2H), 6.98-6.90 (m, 2H), 6.58 (d, 1H, J=5.4 Hz), 3.83 (s, 3H), 3.78 (q, 2H, J=6.1 Hz), 3.43-3.30 (m, 6H), 2.78 (s, 3H).

Example 12. 2-(2-((4-(6-(3-Hydroxylphenyl)imidazo[2,1-b]oxazol-5-yl)pyrimidin-2-yl)amino)ethyl)-5-methyl-1,2,5-thiadiazolidine 1,1-dioxide (1II)

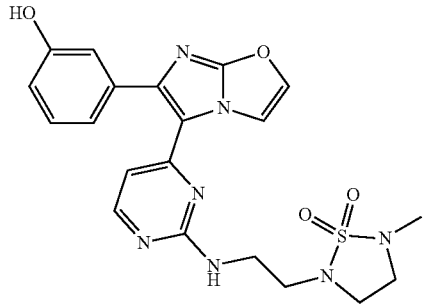 [SMILES: CN1CCN(CCNc2nccc(-c3c(-c4cccc(O)c4)nc4occn34)n2)S1(=O)=O]

Under nitrogen atmosphere, the compound 4I (17.5 mg, 0.1 mmol) was dissolved in 3 mL of MC, and then BBr$_3$ (0.02 mL of 1 M solution in MC, 0.3 mmol) was added dropwise at −78° C., and stirred at the same temperature for 30 minutes, and further stirred at room temperature for 1 hour. After the reaction was completed, a product was dissolved with ethyl acetate, and washed with NaHCO$_3$ and H$_2$O. The organic solvent was dried over MgSO$_4$, followed by filtration. A product was purified by column chromatography (EtOAc:hexane=1:2) to obtain a compound 1II.

White solid (78.1%); mp 151-152° C.; $^1$HNMR (DMSO-d$_6$, 300 MHz) δ 9.56 (s, 1H), 8.12 (d, 1H, J=5.3 Hz), 7.56-7.45 (m, 2H), 7.25 (t, 1H, J=7.9 Hz), 7.00 (s, 1H), 6.97 (d, 2H, J=1.5 Hz), 6.84-6.80 (m, 1H), 6.41 (d, 1H, J=5.3 Hz), 3.71-3.62 (m, 2H), 3.48-3.23 (m, 4H), 3.16 (t, 2H, J=6.0 Hz), 2.60 (s, 3H).

Example 13. 2-Ethyl-5-(2-((4-(6-(3-hydroxylphenyl) imidazo[2,1-b]oxazol-5-yl)pyrimidin-2-yl)amino) ethyl)-1,2,5-thiadiazolidine 1,1-dioxide (2II)

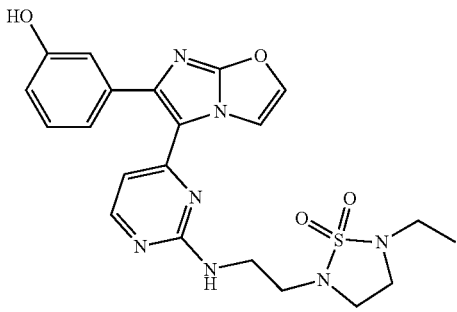 [SMILES: CCN1CCN(CCNc2nccc(-c3c(-c4cccc(O)c4)nc4occn34)n2)S1(=O)=O]

This compound was synthesized in the same manner as in the synthesis of compound 1II.

White solid (66.5%); mp 149-150° C.; $^1$HNMR (DMSO-d$_6$, 300 MHz) δ 9.58 (s, 1H), 8.11 (d, 1H, J=5.4 Hz), 7.56-7.45 (m, 2H), 7.25 (t, 1H, J=8.0 Hz), 6.99-6.80 (m, 3H), 6.41 (d, 1H, J=5.3 Hz), 3.55-3.49 (m, 2H), 3.44-3.23 (m, 4H), 3.19-3.15 (m, 2H), 2.95 (q, 2H, J=7.2 Hz).

Example 14. 2-(2-((4-(6-(3-Hydroxylphenyl)imidazo[2,1-b]oxazol-5-yl)pyrimidin-2-yl)amino)ethyl)-4,4-dimethyl-1,2,5-thiadiazolidine 1,1-dioxide (5II)

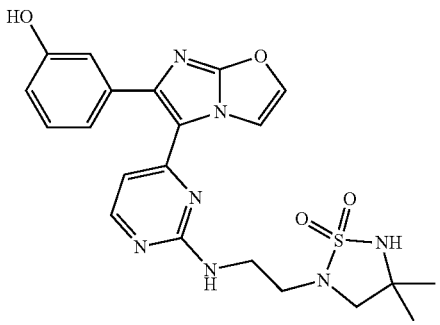 [SMILES: CC1(C)CN(CCNc2nccc(-c3c(-c4cccc(O)c4)nc4occn34)n2)S(=O)(=O)N1]

This compound was synthesized in the same manner as in the synthesis of compound 1II.

White solid (25.0%); mp 196-197° C.; $^1$HNMR (CDCl$_3$, 400 MHz) δ 8.55 (d, 1H, J=5.4 Hz), 8.04 (d, 1H, J=5.4 Hz), 7.30-7.28 (m, 1H), 7.15-7.13 (m, 2H), 6.95 (d, H, J=8.1 Hz), 3.76 (t, 2H, J=6.1 Hz), 3.33 (t, 2H, J=5.92 Hz), 3.25 (s, 2H), 1.45 (s, 6H).

Example 15. 2-(2-((4-(6-(3-Hydroxylphenyl)imidazo[2,1-b]oxazol-5-yl)pyrimidin-2-yl)amino)ethyl)-6-methyl-1,2,6-thiadiazinane 1,1-dioxide (6II)

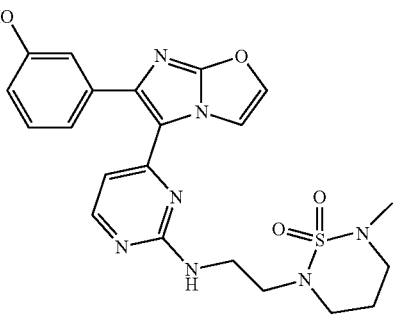

This compound was synthesized in the same manner as in the synthesis of compound 1II.

White solid (71.7%); mp 184-185° C.; $^1$HNMR (CDCl$_3$, 400 MHz) δ 8.57 (d, 1H, J=4.5 Hz), 8.01 (d, 1H, J=5.4 Hz), 7.28-7.26 (m, 1H), 7.15-7.11 (m, 2H), 6.88 (d, H, J=7.7 Hz), 6.59 (d, 1H, J=5.3 Hz), 3.67 (t, 2H, J=5.4 Hz), 3.48 (t, 2H, J=5.2 Hz), 3.37 (t, 2H, J=6.0 Hz), 2.75 (s, 3H), 1.78 (m, 2H).

Example 16. 2-(2-((4-(6-(3-Hydroxylphenyl)imidazo[2,1-b]oxazol-5-yl)pyrimidin-2-yl) amino) ethyl)-1,2,6-thiadiazinane 1,1-dioxide (8II)

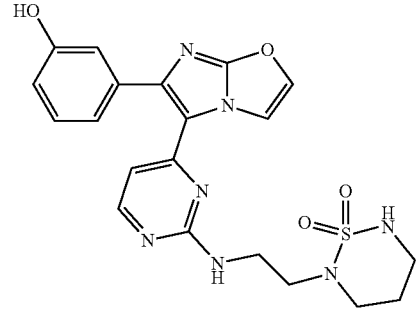 [SMILES: O=S1(=O)NCCCN1CCNc1nccc(-c2c(-c3cccc(O)c3)nc3occn23)n1]

This compound was synthesized in the same manner as in the synthesis of compound 1II.

White solid (85.3%); mp 183-184° C.; $^1$H-NMR (CDCl$_3$, 400 MHz) δ 8.85 (s, 1H), 8.14 (d, 1H, J=5.9 Hz), 7.78 (d, 1H, J=4.1 Hz), 7.47 (t, 1H, J=7.7 Hz), 7.17-7.09 (m, 3H), 6.74 (d, H, J=6.7 Hz), 3.88 (m, 2H), 3.60 (t, 2H, J=7.7 Hz), 3.44-3.41 (m, 4H), 1.78 (m, 2H).

Example 17. 4-Fluoro-N-(2-((4-(6-phenylimidazo[2,1-b]thiazol-5-yl)pyrimidin-2-yl)amino)ethyl)benzenesulfonamide (1III)

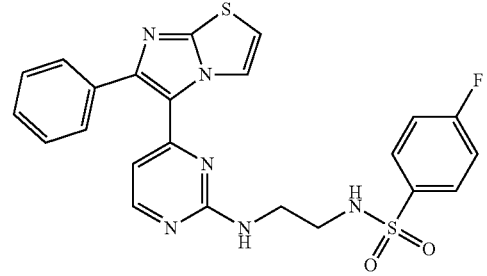 [SMILES: O=S(=O)(NCCNc1nccc(-c2c(-c3ccccc3)nc3sccn23)n1)c1ccc(F)cc1]

Under nitrogen atmosphere, the compound 5d (327 mg, 0.92 mmol), N-(3-aminoethyl)-4-fluorobenzenesulfonamide (11b, 540 mg, 2.48 mmol), and diisopropylethylamine (0.57 mL 3.3 mmol) were added to a DMSO solvent (10 mL), and stirred at 80° C. for 8 hours. After the reaction was completed, a product was extracted with ethyl acetate. An organic solvent layer was dried over MgSO$_4$, and filtered to remove the solvent. A residue was purified by column chromatography (EtOAc) to obtain a compound 1III.

Orange color solid (52.1%); mp. 121-122° C.; $^1$HNMR (DMSO-d$_6$, 300 MHz) b 8.83 (bs, NH), 8.05 (d, 1H, J=6 Hz), 7.80 (dd, 2H, J=6, J=3 Hz), 7.58 (dd, 4H, J=6, J=3 Hz), 7.46 (d, 5H, J=6 Hz), 6.31 (d, 1H, J=6 Hz), 2.96 (t, 2H, J=6 Hz), 2.50 (s, 2H); 13C-NMR (DMSO-d6, 75 MHz) δ 164.2, 162.5, 160.9, 158.2, 156.2, 151.6, 148.0, 140.9, 132.7, 131.7, 129.6, 126.8, 121.0, 115.9, 114.5, 105.7, 38.7, 29.5; LC-MS: Predicted value calculated with respect to $C_{23}H_{19}FN_6O_2S_2$ m/z: 494 Measured value: 495 (M+1)$^+$.

Example 18. 4-Methoxy-N-(2-((4-(6-phenylimidazo[2,1-b]thiazol-5-yl)pyrimidin-2-yl)amino)ethyl)benzenesulfonamide (2III)

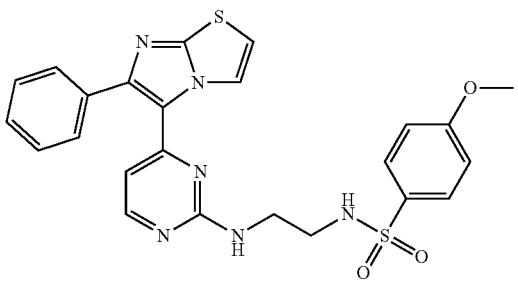 [SMILES: COc1ccc(S(=O)(=O)NCCNc2nccc(-c3c(-c4ccccc4)nc4sccn34)n2)cc1]

This compound was synthesized in the same manner as in the synthesis of compound 1III.

White solid (65%); mp. 199-200° C.; $^1$H-NMR (MeOD, 400 MHz) δ 9-10 (bs, 2NH protons), 8.87 (d, 1H, J=4.8 Hz), 8.50 (d, 2H, J=7.5 Hz), 8.40 (s, 2H), 8.28 (s, 5H), 8.16 (d, 2H, J=7.2 Hz), 7.12 (s, 1H), 3.76 (s, 3H), 3.33 (s, 2H), 3.15 (s, 1H); $^{13}$C NMR (DMSO-d$_6$, 100 MHz) δ 163.8, 162.5, 161.4, 158.1, 156.2, 151.6, 148.1, 142.9, 138.0, 131.7, 130.1, 127.0, 121.0, 115.9, 114.4, 105.7, 55.3, 41.7, 29.5. LC-MS: Predicted value calculated with respect to $C_{24}H_{22}N_6O_2S_2$ m/z: 506 Measured value: 507 (M+1)$^+$.

Example 19. N-(2-((4-(6-(3-methoxyphenyl)imidazo[2,1-b]thiazol-5-yl)pyrimidin-2-yl)amino)ethyl)-4-(trifluoromethyl)benzenesulfonamide (8III)

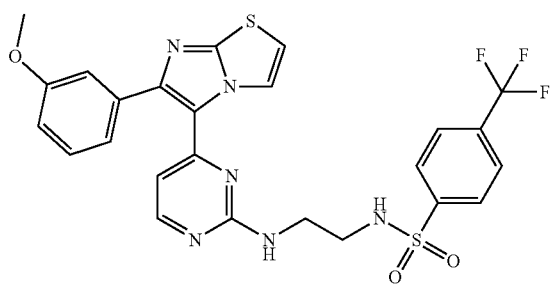 [SMILES: COc1cccc(-c2nc3sccn3c2-c2ccnc(NCCNS(=O)(=O)c3ccc(C(F)(F)F)cc3)n2)c1]

This compound was synthesized in the same manner as in the synthesis of compound 1III.

Colorless sticky oil (25%); $^1$HNMR (DMSO-d$_6$, 400 MHz) δ 8.05 (d, 1H, J=5.2 Hz), 7.73 (t, 2H, J=7.2 Hz), 7.59 (dd, 2H, J=2, J=8 Hz), 7.47 (d, 4H, J=7.2 Hz), 7.06 (d, 2H, J=8.8 Hz), 6.31 (d, 1H, J=5.2 Hz), 3.79 (s, 3H), 3.39 (bs, 2H), 2.94 (brs, 2H). LC-MS: Predicted value calculated with respect to $C_{25}H_{21}F_3N_6O_3S_2$ m/z: 574. Measured value: 575 (M+1)$^+$.

Example 20. 4-Fluoro-N-(2-((4-(6-(3-hydroxyphenyl)imidazo[2,1-b]thiazol-5-yl)pyrimidin-2-yl)amino)ethyl)benzenesulfonamide (25III)

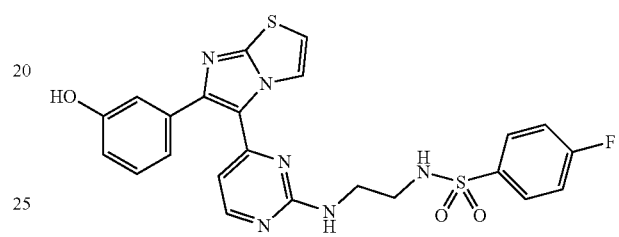

This compound was synthesized in the same manner as in the synthesis of compound 1III.

Dark orange color solid (44%); mp 70-71° C.; IR (KBr) [cm$^{-1}$]: 3115, 2854, 1639, 1574, 1445, 1328; $^1$H-NMR (MeOD, 300) δ 8.68 (s, 1H), 7.87 (t, 3H, J=9 Hz), 7.58-7.45 (m, 6H), 6.97 (d, 3H, J=6 Hz), 6.65 (d, 1H, J=9 Hz), 3.33 (brs, 2H), 3.22 (t, 2H, J=6). LC-MS: Predicted value calculated with respect to $C_{23}H_{20}N_6O_3S_2$ m/z: 492. Measured value: 493 (M+1)$^+$.

Example 21. 4-Fluoro-N-(3-((4-(6-(3-hydroxyphenyl)imidazo[2,1-b]thiazol-5-yl)pyrimidin-2-yl)amino)propyl)benzenesulfonamide (3III)

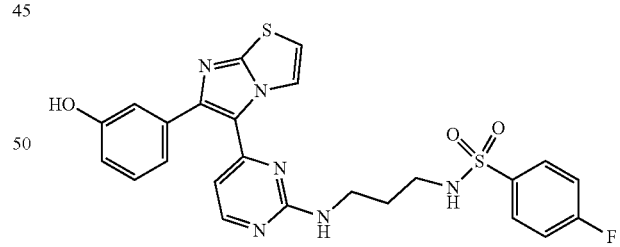

This compound was synthesized in the same manner as in the synthesis of compound 1II.

Lemon yellow color solid (20%); mp 92-93° C.; IR (KBr) [cm$^{-1}$]: 3382, 3258, 3118, 2933, 1731, 1574, 1447, 1331; 1H-NMR (DMSO-d6, 400) δ 9.59 (s, 1H), 8.08 (d, 1H, J=4 Hz), 7.85 (dd, 2H, J=4, J=8 Hz), 7.70 (t, 1H, J=4 Hz), 7.45 (d, 1H, J=4 Hz), 7.40 (t, 3H, J=8 Hz), 7.27 (t, 1H, J=8 Hz), 6.98 (d, 1H, J=4 Hz), 6.84 (d, 1H, J=8 Hz), 6.38 (d, 1H, J=4 Hz), 3.31 (d, 2H, J=4 Hz), 2.85 (q, 2H, J=4 Hz), 1.70 (t, 2H, J=4 Hz). LC-MS: Predicted value calculated with respect to $C_{24}H_{21}FN_6O_3S_2$ m/z: 524. Measured value: 525 (M+1)$^+$.

The other compounds were synthesized in the same manner as in the synthesis of compound 1I, compound 1II, or compound III, except that different substituents were used. Examples of the synthesized compounds are as shown in the following Table 1.

TABLE 1

| Compound No. | Structure | Compound No. | Structure |
|---|---|---|---|
| 1I | (structure) | 2I | (structure) |
| 3I | (structure) | 4I | (structure) |
| 5I | (structure) | 6I | (structure) |

TABLE 1-continued

| Compound No. | Structure | Compound No. | Structure |
|---|---|---|---|
| 7I | 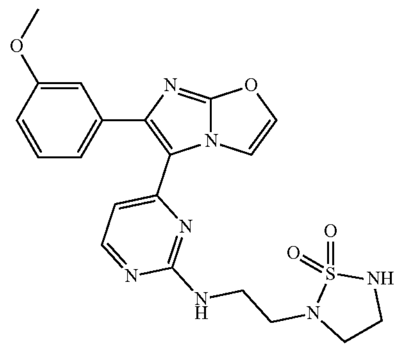 | 8I | 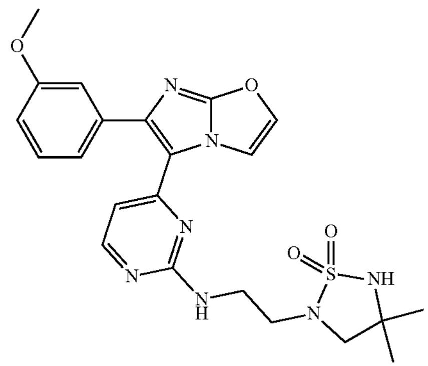 [SMILES: COc1cccc(-c2nc3occn3c2-c2ccnc(NCCN3CC(C)(C)NS3(=O)=O)n2)c1] |
| 9I | 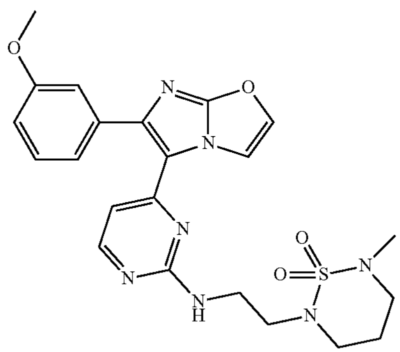 [SMILES: COc1cccc(-c2nc3occn3c2-c2ccnc(NCCN3CCCN(C)S3(=O)=O)n2)c1] | 10I | 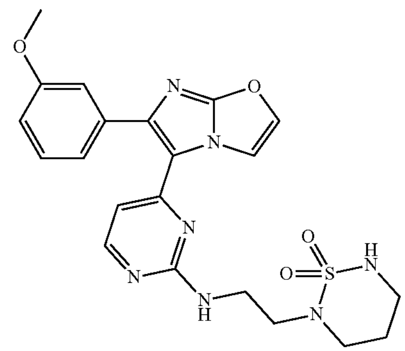 [SMILES: COc1cccc(-c2nc3occn3c2-c2ccnc(NCCN3CCCNS3(=O)=O)n2)c1] |
| 11I | 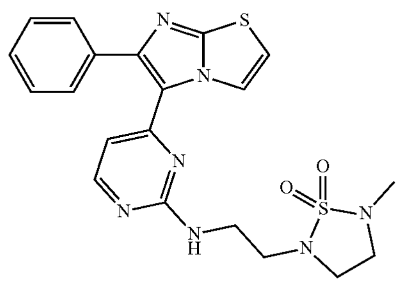 [SMILES: CN1CCN(CCNc2nccc(-c3c(-c4ccccc4)nc4sccn34)n2)S1(=O)=O] | 12I | 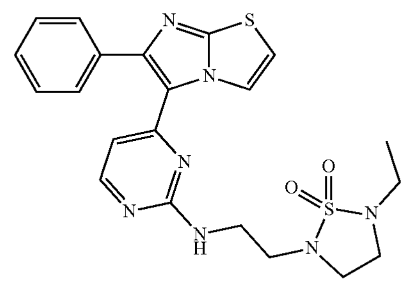 [SMILES: CCN1CCN(CCNc2nccc(-c3c(-c4ccccc4)nc4sccn34)n2)S1(=O)=O] |

TABLE 1-continued

| Compound No. | Structure | Compound No. | Structure |
|---|---|---|---|
| 13I | 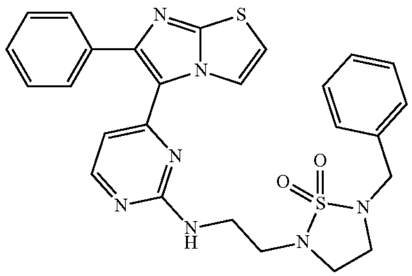 [SMILES: O=S1(=O)N(CCNc2nccc(-c3c(-c4ccccc4)nc4sccn34)n2)CCN1Cc1ccccc1] | 14I | 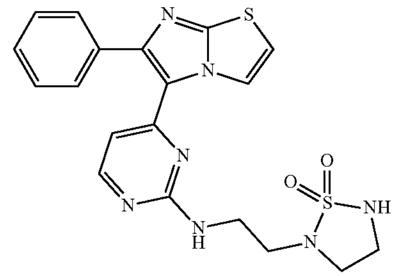 [SMILES: O=S1(=O)NCCN1CCNc1nccc(-c2c(-c3ccccc3)nc3sccn23)n1] |
| 15I | 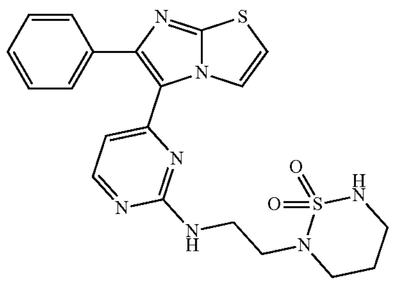 [SMILES: O=S1(=O)NCCCN1CCNc1nccc(-c2c(-c3ccccc3)nc3sccn23)n1] | 16I | 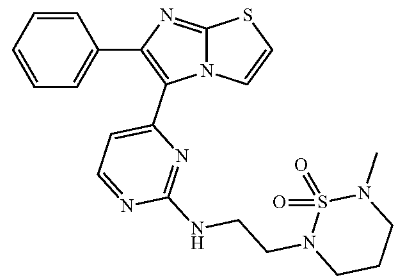 [SMILES: CN1CCCN(CCNc2nccc(-c3c(-c4ccccc4)nc4sccn34)n2)S1(=O)=O] |
| 17I | 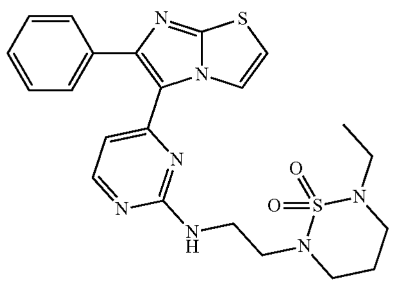 [SMILES: CCN1CCCN(CCNc2nccc(-c3c(-c4ccccc4)nc4sccn34)n2)S1(=O)=O] | 18I | 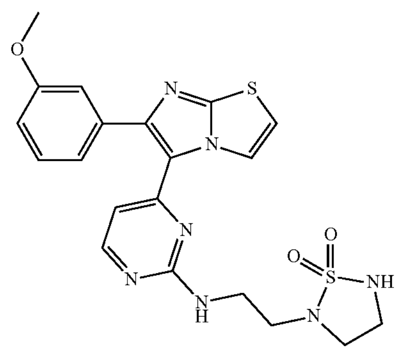 |

TABLE 1-continued

| Compound No. | Structure | Compound No. | Structure |
|---|---|---|---|
| 191 | | 201 | |
| 211 | | 221 | |
| 231 | | 241 | |

TABLE 1-continued

| Compound No. | Structure |
|---|---|
| 1II | (structure) |
| 2II | (structure) |
| 3II | (structure) |
| 4II | (structure) |
| 5II | (structure) |
| 6II | (structure) |

TABLE 1-continued
| Compound No. | Structure | Compound No. | Structure |
|---|---|---|---|
| 7II | 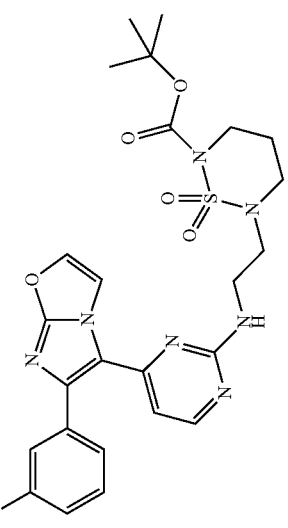 | 8II | 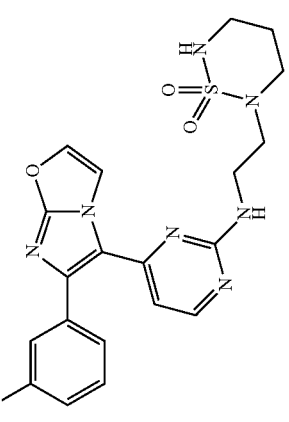 |
| 9II | 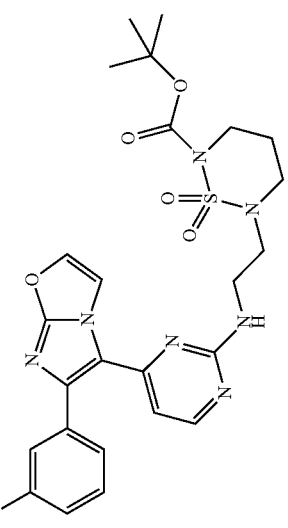 | 10II | 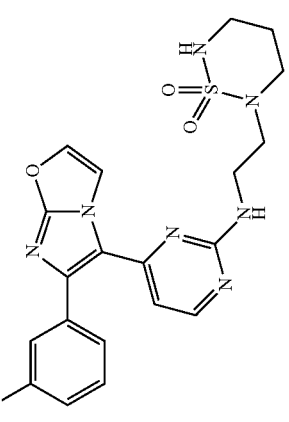 |
| 11II | 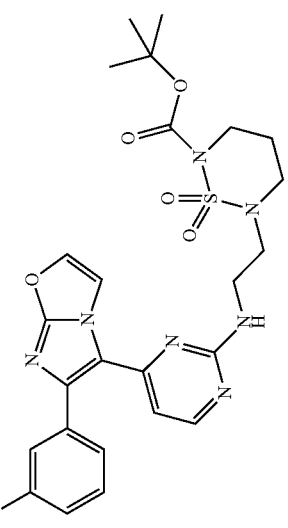 | 12II | 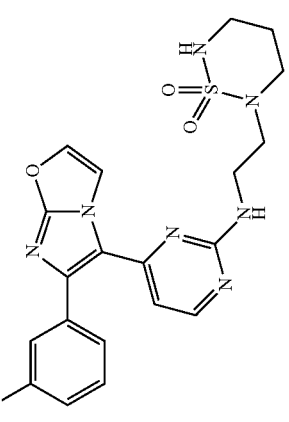 |

TABLE 1-continued

| Compound No. | Structure | Compound No. | Structure |
|---|---|---|---|
| 13II | 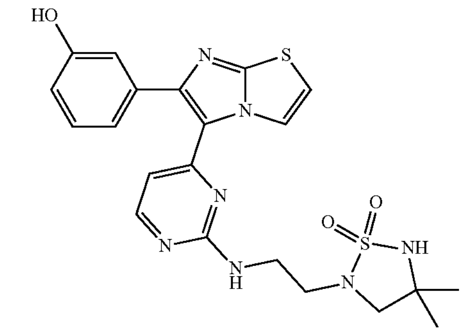 [SMILES: CC1(C)CN(CCNc2nccc(-c3c(-c4cccc(O)c4)nc4sccn34)n2)S(=O)(=O)N1] | 14II | 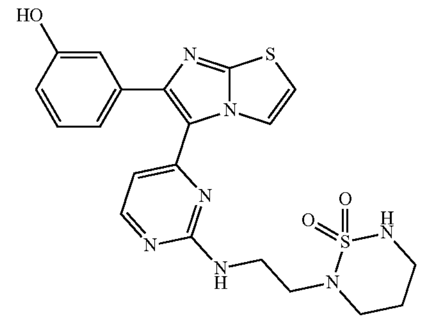 [SMILES: O=S1(=O)NCCCN1CCNc1nccc(-c2c(-c3cccc(O)c3)nc3sccn23)n1] |
| 15II | 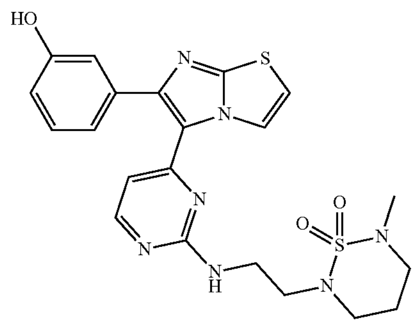 [SMILES: CN1CCCN(CCNc2nccc(-c3c(-c4cccc(O)c4)nc4sccn34)n2)S1(=O)=O] | 16II | 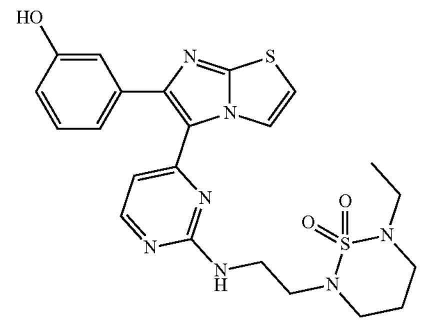 [SMILES: CCN1CCCN(CCNc2nccc(-c3c(-c4cccc(O)c4)nc4sccn34)n2)S1(=O)=O] |
| 1III | 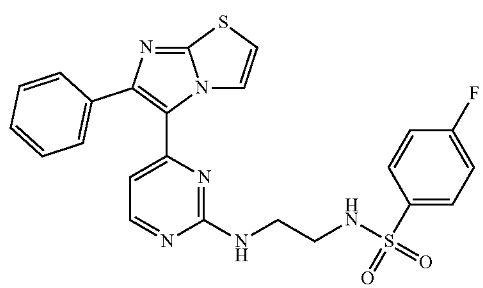 [SMILES: O=S(=O)(NCCNc1nccc(-c2c(-c3ccccc3)nc3sccn23)n1)c1ccc(F)cc1] | 2III | 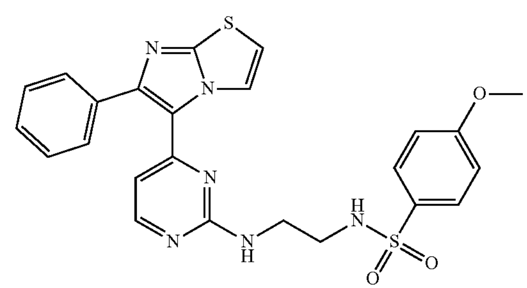 [SMILES: COc1ccc(S(=O)(=O)NCCNc2nccc(-c3c(-c4ccccc4)nc4sccn34)n2)cc1] |

TABLE 1-continued

| Compound No. | Structure | Compound No. | Structure |
|---|---|---|---|
| 3III | (structure) | 4III | (structure) |
| 5III | (structure) | 6III | (structure) |
| 7III | (structure) | 8III | (structure) |

TABLE 1-continued

| Compound No. | Structure |
|---|---|
| 9III | (structure) |
| 10III | (structure) |
| 11III | (structure) |
| 12III | (structure) |
| 13III | (structure) |
| 14III | (structure) |

TABLE 1-continued

| Compound No. | Structure | Compound No. | Structure |
|---|---|---|---|
| 15III | (structure) | 16III | (structure) |
| 17III | (structure) | 18III | (structure) |
| 19III | (structure) | 20III | (structure) |

TABLE 1-continued

| Compound No. | Structure | Compound No. | Structure |
|---|---|---|---|
| 21III | 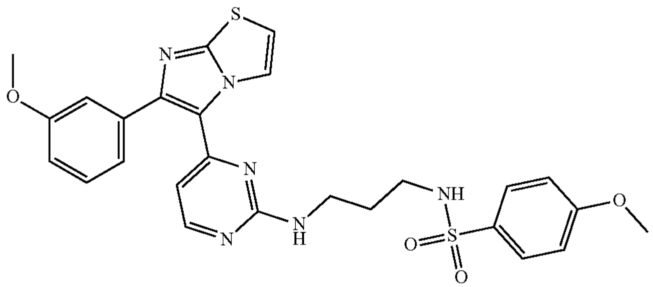 [SMILES: COc1ccc(S(=O)(=O)NCCCNc2nccc(-c3c(-c4cccc(OC)c4)nc4sccn34)n2)cc1] | 22III | 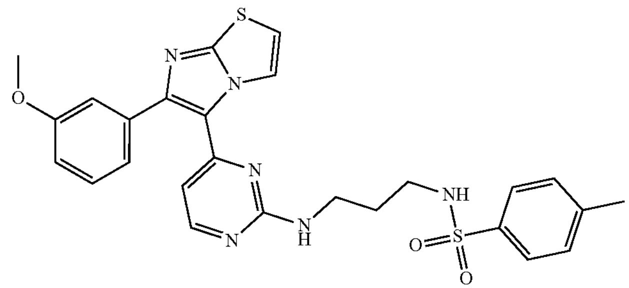 [SMILES: COc1cccc(-c2nc3sccn3c2-c2ccnc(NCCCNS(=O)(=O)c3ccc(C)cc3)n2)c1] |
| 23III | 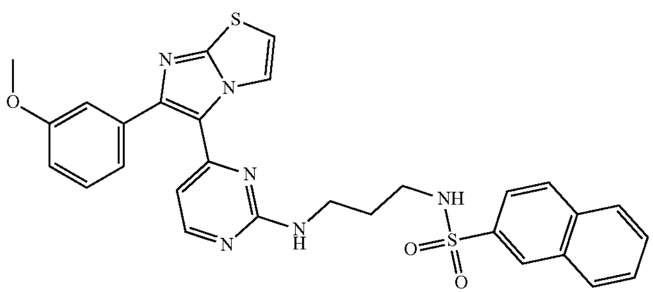 [SMILES: COc1cccc(-c2nc3sccn3c2-c2ccnc(NCCCNS(=O)(=O)c3ccc4ccccc4c3)n2)c1] | 24III | 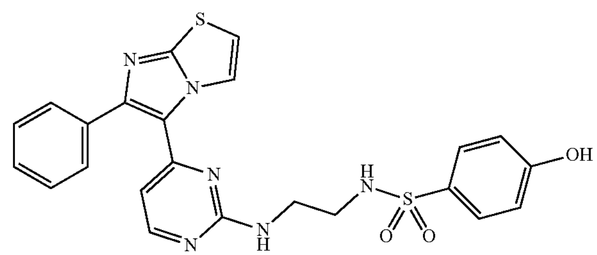 [SMILES: O=S(=O)(NCCNc1nccc(-c2c(-c3ccccc3)nc3sccn23)n1)c1ccc(O)cc1] |
| 25III | 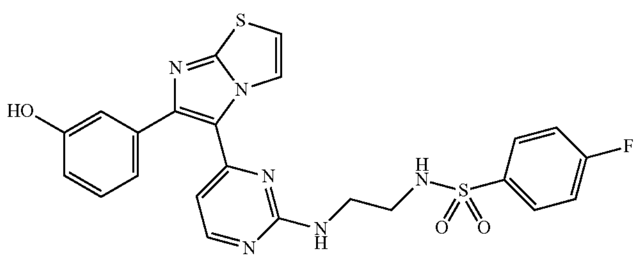 [SMILES: O=S(=O)(NCCNc1nccc(-c2c(-c3cccc(O)c3)nc3sccn23)n1)c1ccc(F)cc1] | 26III | 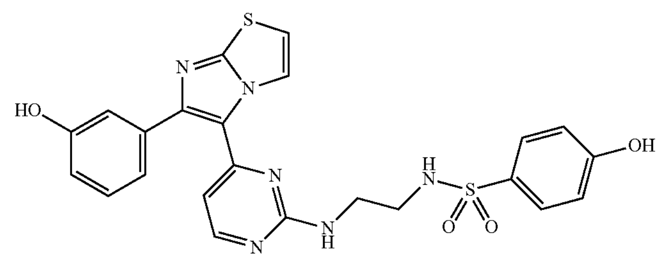 [SMILES: O=S(=O)(NCCNc1nccc(-c2c(-c3cccc(O)c3)nc3sccn23)n1)c1ccc(O)cc1] |

TABLE 1-continued
| Compound No. | Structure | Compound No. | Structure |
|---|---|---|---|
| 27III | 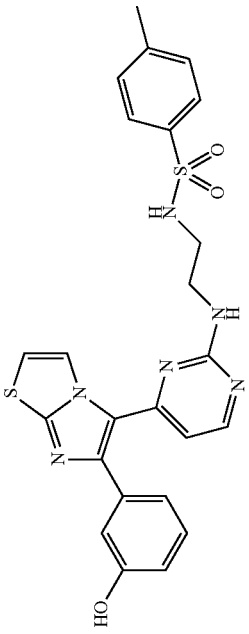 | 28III | 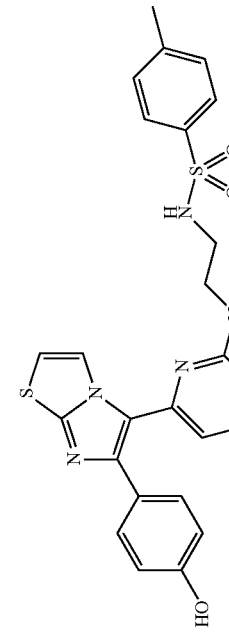 |
| 29III | 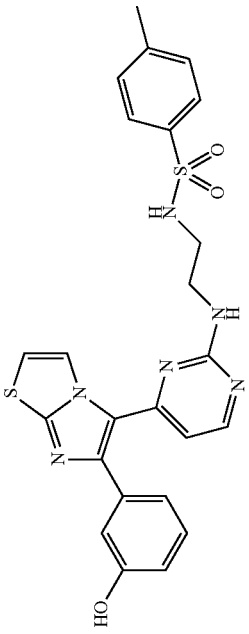 | 30III | 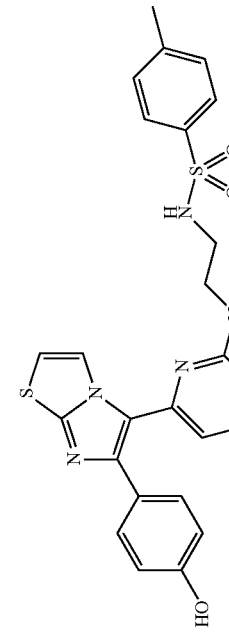 |
| 31III | 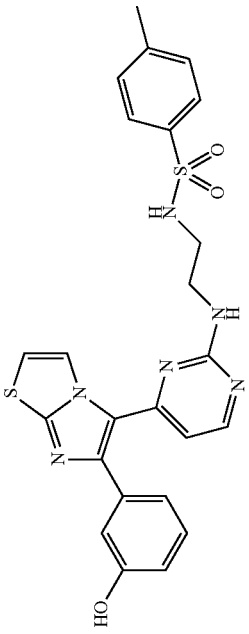 | 1IV | 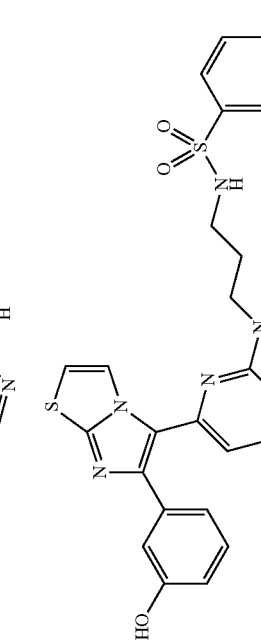 |

TABLE 1-continued

| Compound No. | Structure | Compound No. | Structure |
|---|---|---|---|
| 2IV | 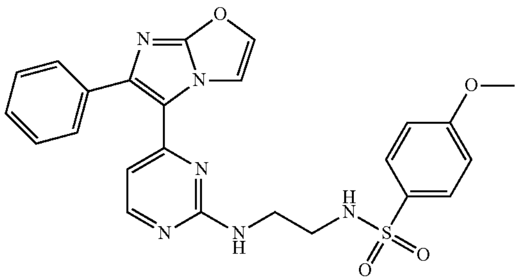 [SMILES: COc1ccc(S(=O)(=O)NCCNc2nccc(-c3c(-c4ccccc4)nc4occn34)n2)cc1] | 3IV | 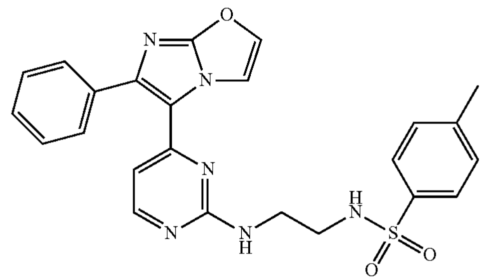 [SMILES: Cc1ccc(S(=O)(=O)NCCNc2nccc(-c3c(-c4ccccc4)nc4occn34)n2)cc1] |
| 4IV | 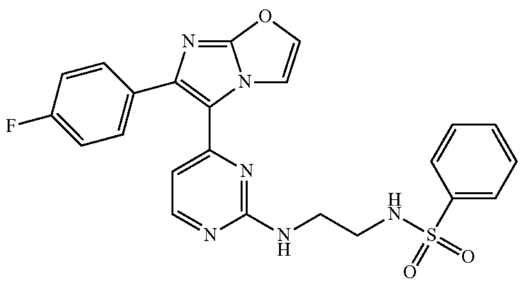 [SMILES: O=S(=O)(NCCNc1nccc(-c2c(-c3ccc(F)cc3)nc3occn23)n1)c1ccccc1] | 5IV | 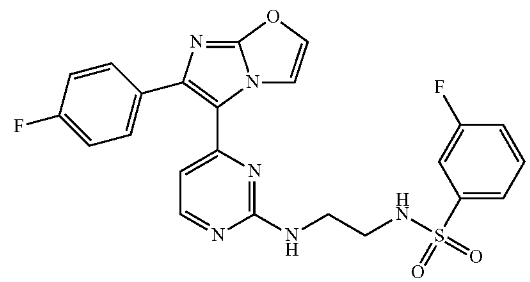 [SMILES: O=S(=O)(NCCNc1nccc(-c2c(-c3ccc(F)cc3)nc3occn23)n1)c1cccc(F)c1] |
| 6IV | 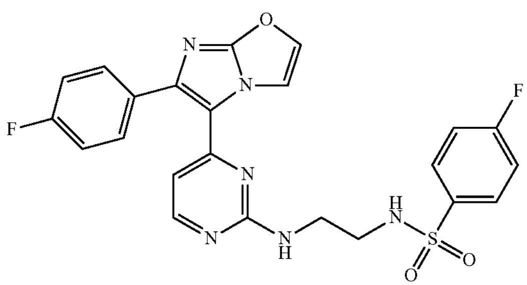 | 7IV | 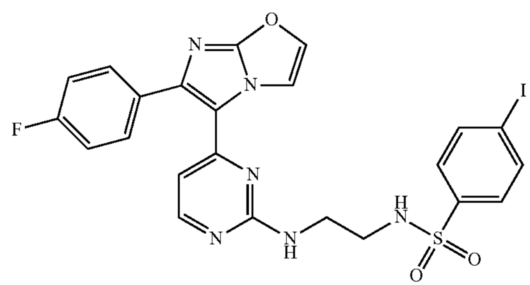 [SMILES: O=S(=O)(NCCNc1nccc(-c2c(-c3ccc(F)cc3)nc3occn23)n1)c1ccc(F)cc1] |

TABLE 1-continued

| Compound No. | Structure | Compound No. | Structure |
|---|---|---|---|
| 8IV | 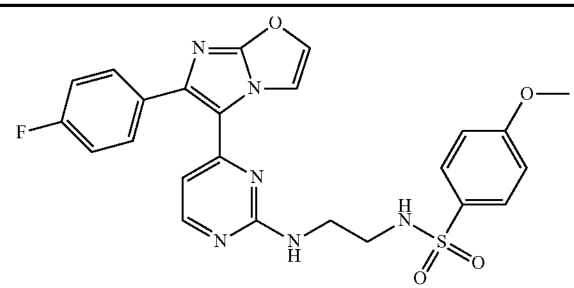 | 9IV | 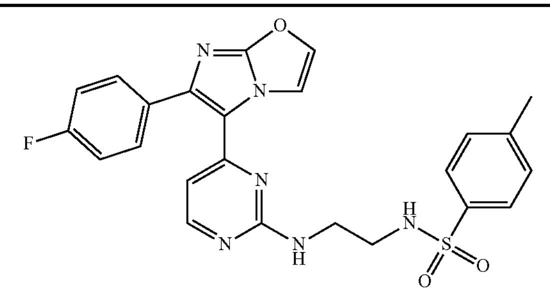 |
| 10IV | 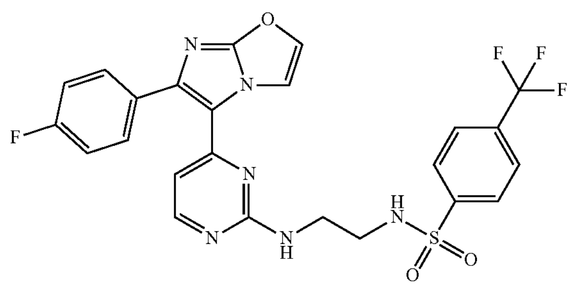 [SMILES: O=S(=O)(NCCNc1nccc(-c2c(-c3ccc(F)cc3)nc3occn23)n1)c1ccc(C(F)(F)F)cc1] | 11IV | 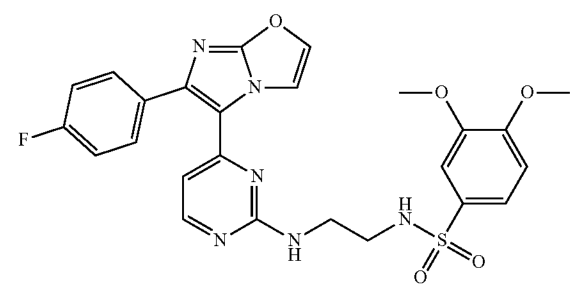 [SMILES: COc1ccc(S(=O)(=O)NCCNc2nccc(-c3c(-c4ccc(F)cc4)nc4occn34)n2)cc1OC] |
| 12IV | 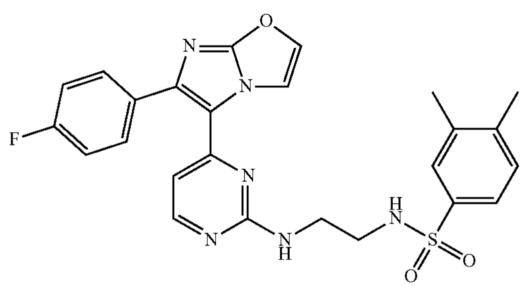 [SMILES: Cc1ccc(S(=O)(=O)NCCNc2nccc(-c3c(-c4ccc(F)cc4)nc4occn34)n2)cc1C] | 13IV | 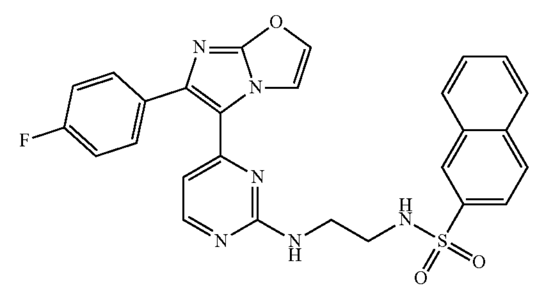 [SMILES: O=S(=O)(NCCNc1nccc(-c2c(-c3ccc(F)cc3)nc3occn23)n1)c1ccc2ccccc2c1] |

TABLE 1-continued

| Compound No. | Structure |
|---|---|
| 14IV | (structure) |
| 15IV | (structure) |
| 16IV | (structure) |
| 17IV | (structure) |
| 18IV | (structure) |
| 19IV | (structure) |

TABLE 1-continued

| Compound No. | Structure |
|---|---|
| 20IV | (structure) |
| 21IV | (structure) |
| 22IV | (structure) |
| 23IV | (structure) |
| 24IV | (structure) |
| 25IV | (structure) |

TABLE 1-continued

| Compound No. | Structure | Compound No. | Structure |
|---|---|---|---|
| 26IV | 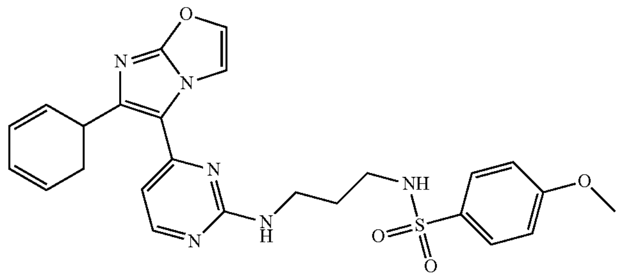 [SMILES: COc1ccc(S(=O)(=O)NCCCNc2nccc(-c3c(C4C=CC=CC4)nc4occn34)n2)cc1] | 27IV | 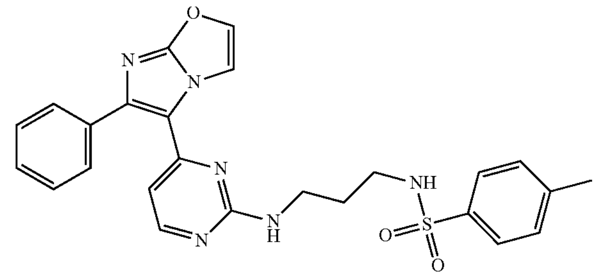 [SMILES: Cc1ccc(S(=O)(=O)NCCCNc2nccc(-c3c(-c4ccccc4)nc4occn34)n2)cc1] |
| 28IV | 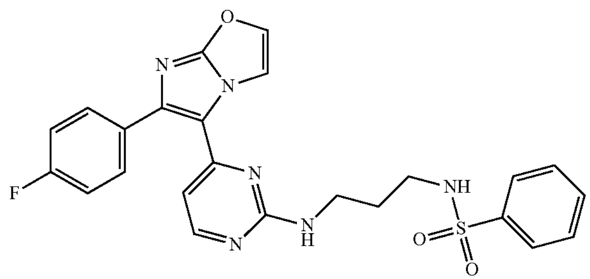 [SMILES: O=S(=O)(NCCCNc1nccc(-c2c(-c3ccc(F)cc3)nc3occn23)n1)c1ccccc1] | 29IV | 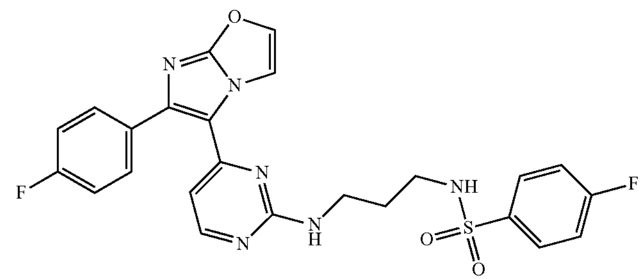 |
| 30IV | 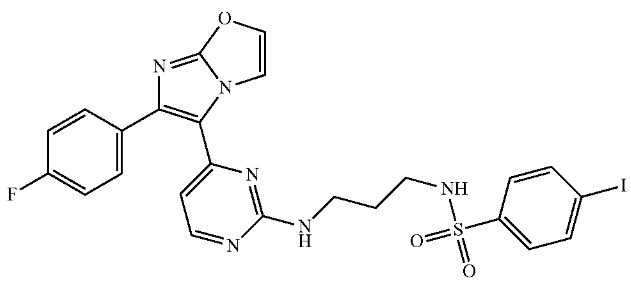 [SMILES: O=S(=O)(NCCCNc1nccc(-c2c(-c3ccc(F)cc3)nc3occn23)n1)c1ccc(F)cc1] | 31IV | 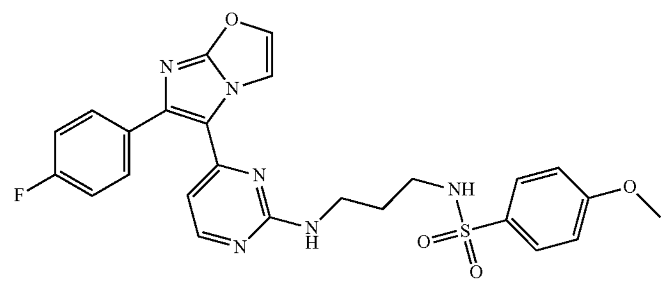 [SMILES: COc1ccc(S(=O)(=O)NCCCNc2nccc(-c3c(-c4ccc(F)cc4)nc4occn34)n2)cc1] |

TABLE 1-continued

| Compound No. | Structure | Compound No. | Structure |
|---|---|---|---|
| 32IV | 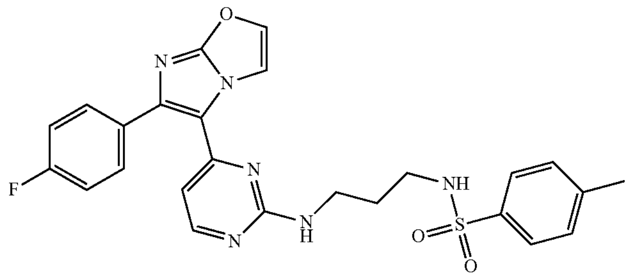 [SMILES: Cc1ccc(S(=O)(=O)NCCCNc2nccc(-c3c(-c4ccc(F)cc4)nc4occn34)n2)cc1] | 33IV | 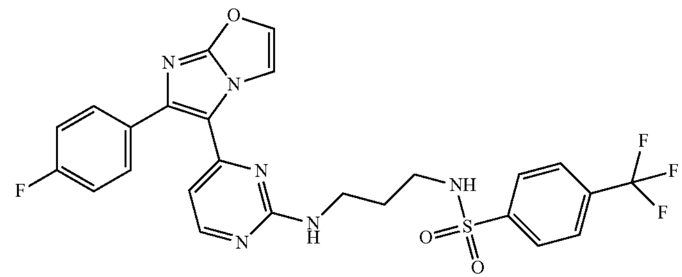 [SMILES: O=S(=O)(NCCCNc1nccc(-c2c(-c3ccc(F)cc3)nc3occn23)n1)c1ccc(C(F)(F)F)cc1] |
| 34IV | 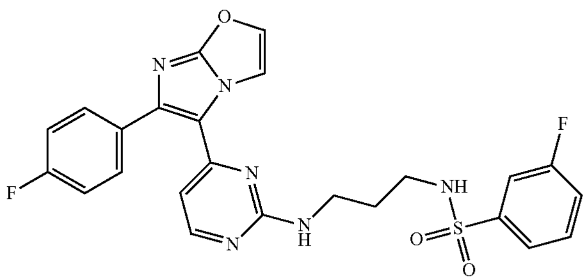 [SMILES: O=S(=O)(NCCCNc1nccc(-c2c(-c3ccc(F)cc3)nc3occn23)n1)c1cccc(F)c1] | 35IV | 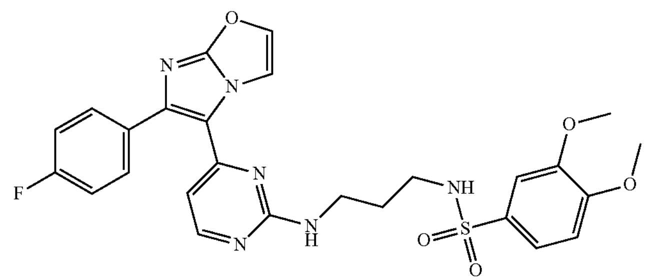 [SMILES: COc1ccc(S(=O)(=O)NCCCNc2nccc(-c3c(-c4ccc(F)cc4)nc4occn34)n2)cc1OC] |
| 36IV | 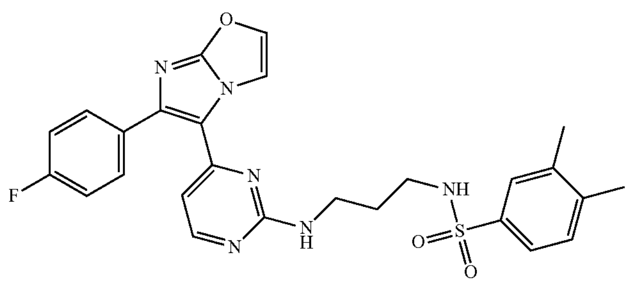 [SMILES: Cc1ccc(S(=O)(=O)NCCCNc2nccc(-c3c(-c4ccc(F)cc4)nc4occn34)n2)cc1C] | 37IV | 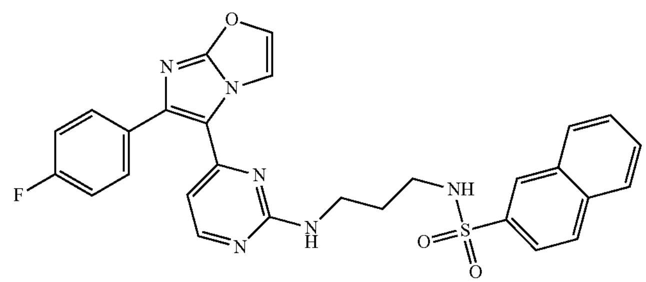 [SMILES: O=S(=O)(NCCCNc1nccc(-c2c(-c3ccc(F)cc3)nc3occn23)n1)c1ccc2ccccc2c1] |

TABLE 1-continued
| Compound No. | Structure | Compound No. | Structure |
|---|---|---|---|
| 38IV | 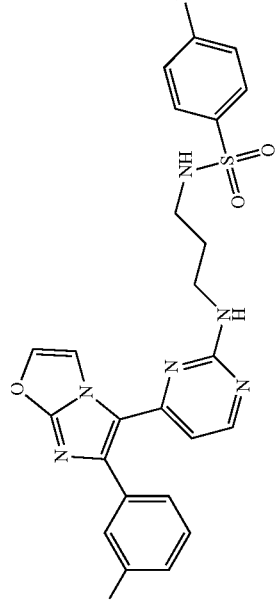 | 39IV | 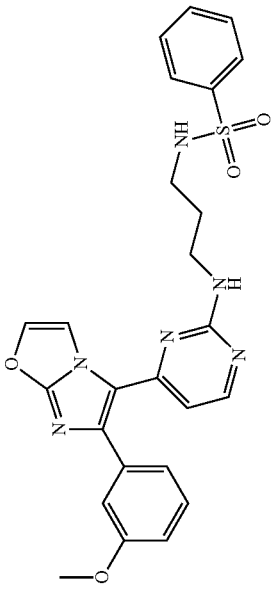 |
| 40IV | 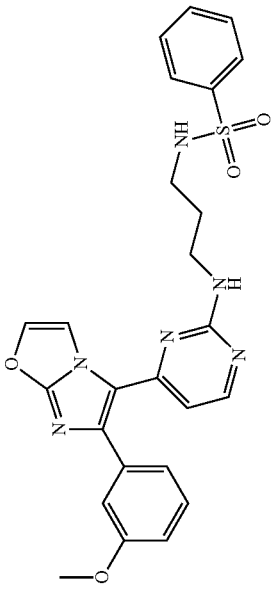 | 41IV | 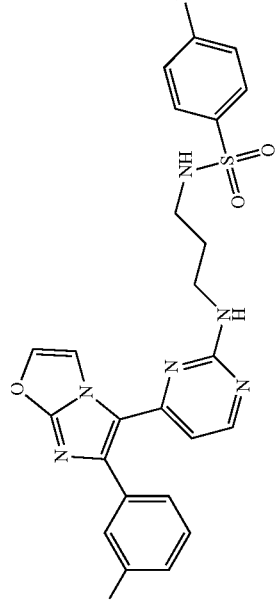 |
| 42IV | 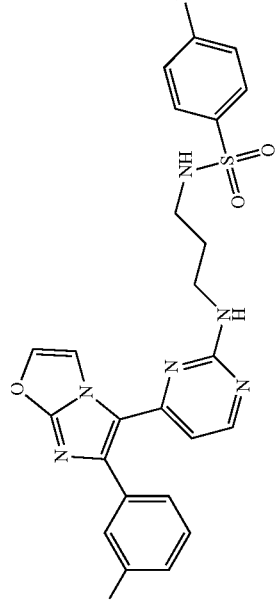 | 43IV | 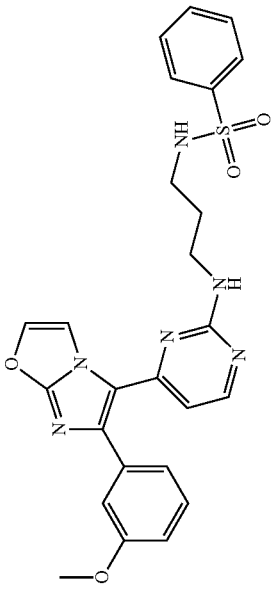 |

TABLE 1-continued

| Compound No. | Structure | Compound No. | Structure |
|---|---|---|---|
| 44IV | 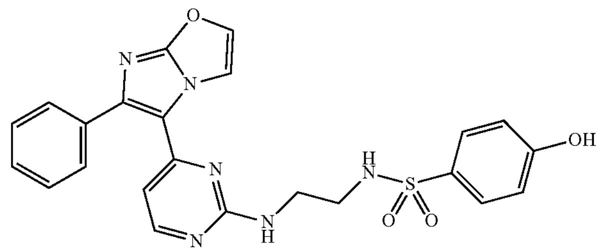 [SMILES: O=S(=O)(NCCNc1nccc(-c2c(-c3ccccc3)nc3occn23)n1)c1ccc(O)cc1] | 45IV | 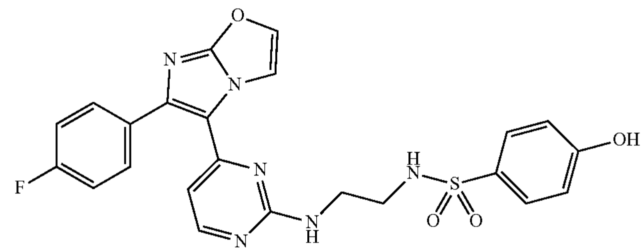 [SMILES: O=S(=O)(NCCNc1nccc(-c2c(-c3ccc(F)cc3)nc3occn23)n1)c1ccc(O)cc1] |
| 46IV | 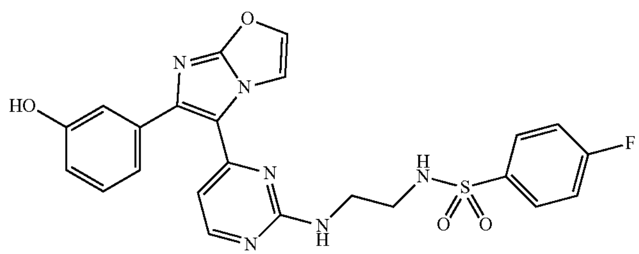 [SMILES: O=S(=O)(NCCNc1nccc(-c2c(-c3cccc(O)c3)nc3occn23)n1)c1ccc(F)cc1] | 47IV | 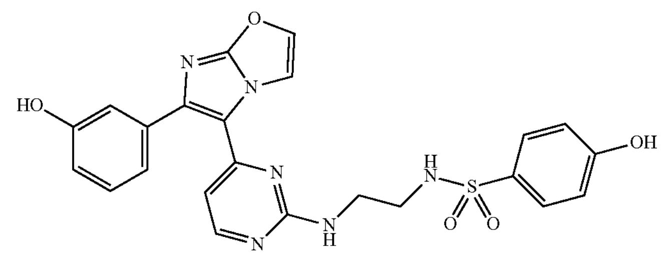 [SMILES: O=S(=O)(NCCNc1nccc(-c2c(-c3cccc(O)c3)nc3occn23)n1)c1ccc(O)cc1] |
| 48IV | 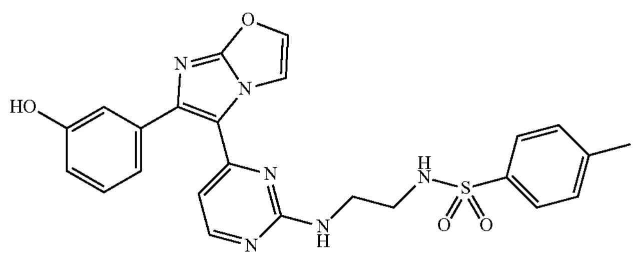 [SMILES: Cc1ccc(S(=O)(=O)NCCNc2nccc(-c3c(-c4cccc(O)c4)nc4occn34)n2)cc1] | 49IV | 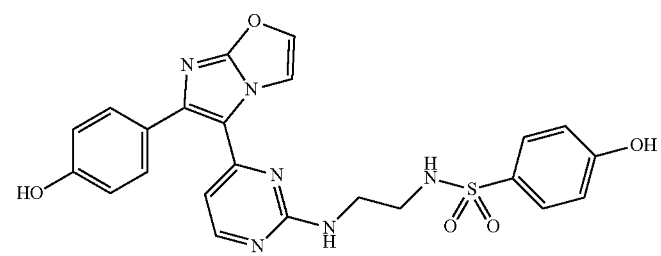 [SMILES: O=S(=O)(NCCNc1nccc(-c2c(-c3ccc(O)cc3)nc3occn23)n1)c1ccc(O)cc1] |

TABLE 1-continued
| Compound No. | Structure | Compound No. | Structure |
|---|---|---|---|
| 50IV | 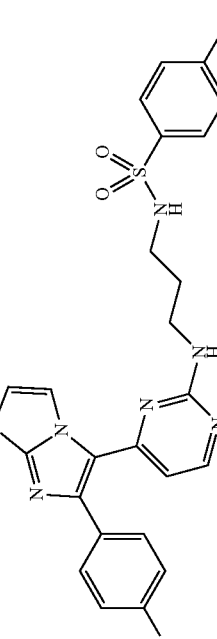 | 51IV | 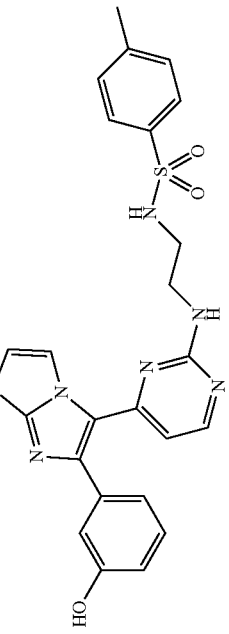 |
| 52IV | 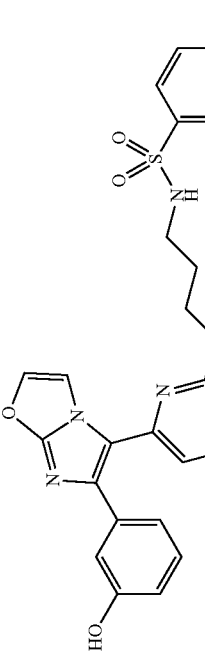 | 53IV | 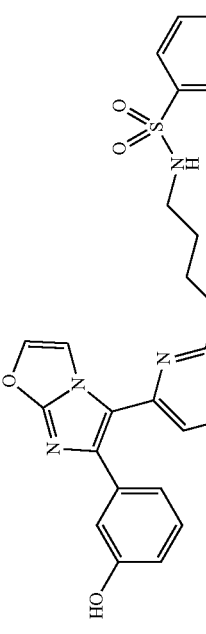 |

<Experimental Example 1> Measurement of Antiproliferative Activity Against Melanoma Cell Lines To measure inhibitory activities of imidazooxazole- or imidazothiazole-based compounds according to the present disclosure against proliferation of cancer cells at a cell level, the following experiments were carried out.

(1) Screening of Cancer Cell Line

According to the standard protocol (http://dtp.nci.nih.gov/dtpstandard/dwindex/index.isp) of the US National Cancer Institute (NCI) (www.dtp.nci.nih.gov), screening of a cancer cell line panel was performed. Briefly, human cell lines were allowed to grow in an RPMI 1640 medium containing 5% FBS and 2 mM L-glutamine. For a general screening experiment, cells were inoculated in 96-well microtiter plates in 100 µl at a plating density ranging from 5000 cells/well to 40,000 cells/well depending on the doubling time of individual cell lines. After cell inoculation, the microtiter plates were incubated at 37° C., 5% $CO_2$, 95% air, and 100% relative humidity for 24 hours prior to addition of test compounds. 24 hours later, two plates of each cell line were fixed in situ with trichloroacetic acid (TCA) to measure the cell population for each cell line at the time of test compound addition (Tz). Test compounds were solubilized in dimethyl sulfoxide at 400-fold the intended final maximum test concentration, and stored frozen prior to use. At the time of compound addition, an aliquot of frozen concentrate was thawed and diluted to twice the intended final maximum test concentration with a complete medium containing 50 µg/ml of gentamicin. Additional four concentration of 10-fold or ½ log serial dilutions were made to provide a total of five compound concentrations plus control. Aliquots of 100 µl of these different compound dilutions were added to appropriate microtiter wells already containing 100 µl of medium, resulting in the required final compound concentrations.

Following compound addition, the plates were incubated for additional 48 hours at 37° C., 5% $CO_2$, 95% air, and 100% relative humidity. For adherent cells, the assay was terminated by the addition of cold TCA. Cells were fixed in situ by the gentle addition of 50 µl of cold 50% (w/v) TCA (final concentration, 10% TAC) and incubated at 4° C. for 60 minutes. The supernatant was discarded, and the plates were washed five times with tap water and air-dried. A sulforhodamine B (SRB) solution (100 µl) at 0.4% (w/v) in 1% acetic acid was added to each well, and plates were incubated at room temperature for 10 minutes. After staining, unbound dye was removed by washing five times with 1% acetic acid and the plates were air-dried. Bound stain was subsequently solubilized with 10 mM Trizma base, and the absorbance was read on an automated plate reader at a wavelength of 515 nm. For suspension cells, the methodology was the same except that the assay was terminated by fixing settled cells at the bottom of the wells by gently adding 50 µl of 80% TCA (final concentration, 16% TCA). Using the seven absorbance measurements [time zero (Tz), control growth (C), and test growth rate in the presence of compound at the five concentration levels (Ti)], the growth percentage was calculated at each of the compound concentration levels. Growth inhibition percentage was calculated as follows:

$[(Ti-Tz)/(C-Tz)] \times 100$ for concentrations for which $Ti >/= Tz$ $[(Ti-Tz)/Tz] \times 100$ for concentrations for which $Ti < Tz$.

TABLE 2

| | IC$_{50}$ values of main compounds against melanoma cell lines in vitro | | | | | | | | |
|---|---|---|---|---|---|---|---|---|---|
| | 1II | 2II | 5II | 6II | 8II | 2III | 8III | 25III | 31III |
| A375 | 0.06 | 0.19 | 0.87 | 0.47 | 0.058 | ND | ND | 0.48 | 0.30 |
| LOX IMVI | ND | 2.53 | 2.30 | 4.36 | 2.15 | 3.94 | 3.26 | 4.11 | 0.56 |
| M14 | ND | 0.14 | 0.32 | 0.16 | 0.30 | 2.77 | 3.26 | 0.56 | 0.06 |
| MDA-MB-435 | ND | 0.37 | 0.74 | 0.49 | 0.38 | 1.22 | 3.26 | 0.93 | 0.24 |
| SK-MEL-2 | ND | 2.60 | 1.6 | 2.28 | 0.38 | 4.98 | 3.04 | 4.49 | 1.1 |
| SK-MEL-28 | ND | 0.13 | 0.22 | 0.24 | 0.17 | 5.79 | 3.68 | 0.66 | 0.05 |
| SK-MEL-5 | ND | 6.28 | 0.34 | 0.24 | 0.17 | 1.68 | 1.24 | 1.61 | 1.2 |
| UACC-62 | ND | 0.07 | 0.09 | 0.058 | 0.059 | 1.17 | 0.48 | 0.26 | 0.02 |

The test compounds showed proliferation-inhibitory activities against most of the melanoma cell lines shown in Table 2 (all 10 µM or less), indicating that the imidazooxazole- or imidazothiazole-based compounds according to the present disclosure have excellent inhibitory activities against melanoma.

(2) Comparison of Inhibitory Activity Against Proliferation of A375P Melanoma Cell Line To examine whether the compounds (2II, 9II, 10II, and 12II to 15II) of the present disclosure have remarkable effects, as compared with imidazothiazole-based compounds previously disclosed by the present inventors (M. S. Abdel-Maksoud et al./European Journal of Medicinal Chemistry 95 (2015) 453-463), inhibitory activities thereof against proliferation of A375P cell line which is a melanoma cell line were compared by the following experiments.

A375P cell line purchased from ATCC was cultured in a DMEM medium [containing 10% FBS and 1% penicillin/streptomycin] under 5% $CO_2$ at 37° C. The cultured A375P cell line was collected using 0.05% trypsin-0.02% EDTA, and inoculated at a cell density of $5 \times 10^3$ cells per well in a 96-well plate. To measure cell viability, MTT [3-(4,5-dimethylthiazol-2-yl)-2,5-diphenyltetrazolium bromide] assay (CellTiter 96 Assay, Promega) was performed as follows. MTT assay was performed in accordance with the guidelines of CellTiter 96® (Promega). EnVision 2103 was used to read a value at a wavelength of 590 nm, and IC$_{50}$ was calculated using a software of GraphPad Prism 4.0.

TABLE 3
Inhibitory activities (IC$_{50}$ values (μM)) of main imidazothiazole-based compounds against proliferation of A375P cell line
| Compound | IC$_{50}$ (A375P) |
| --- | --- |
| 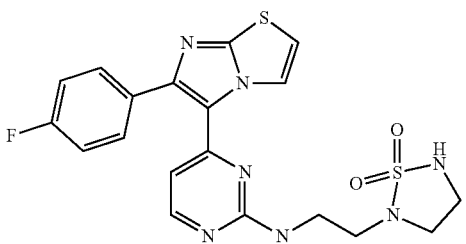 P1 | 1.90 |
| 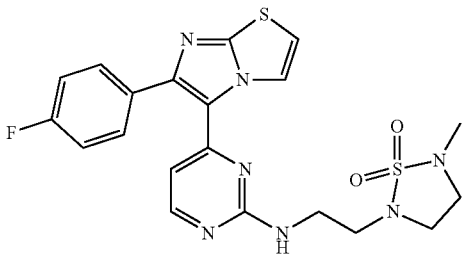 P2 | 0.60 |
| 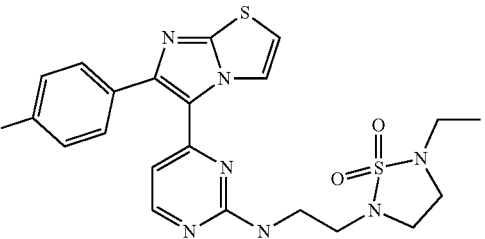 P3 | 0.38 |
| 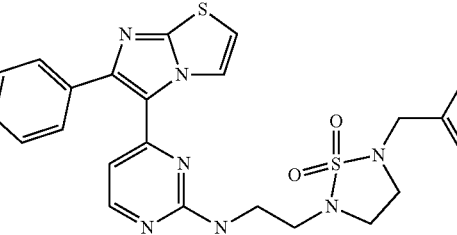 P4 | >10 |
| 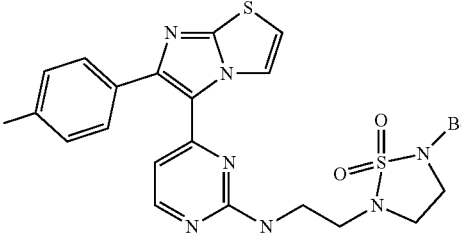 P5 | >10 |

TABLE 3-continued
Inhibitory activities (IC$_{50}$ values (μM)) of main imidazothiazole-based compounds against proliferation of A375P cell line
| Compound | IC$_{50}$ (A375P) |
|---|---|
| 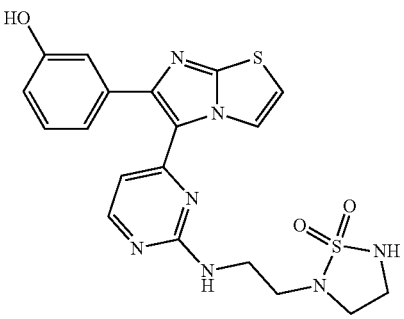 9II | 0.63 |
| 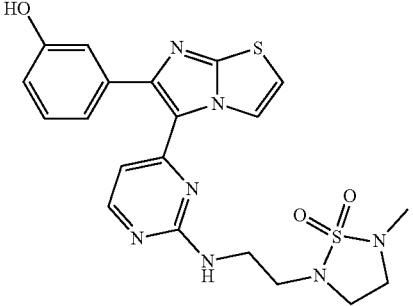 10II | 0.06 |
| 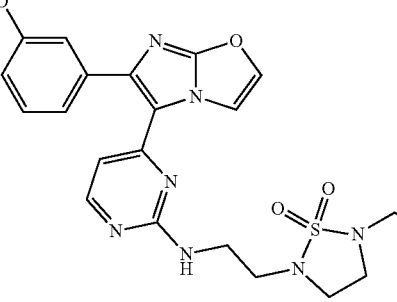 2II | 0.19 |
| 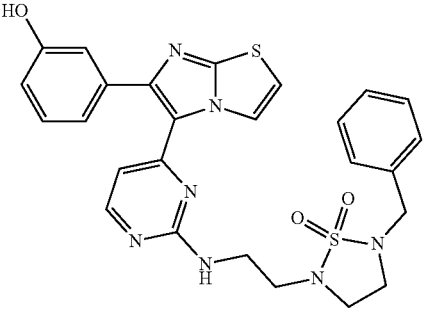 12II | 0.25 |

TABLE 3-continued
Inhibitory activities (IC$_{50}$ values (μM)) of main imidazothiazole-based compounds against proliferation of A375P cell line
| Compound | IC$_{50}$ (A375P) |
| --- | --- |
| 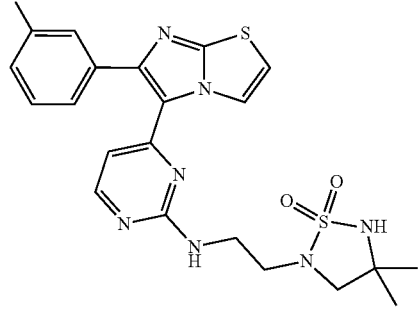 13II | 0.87 |
| 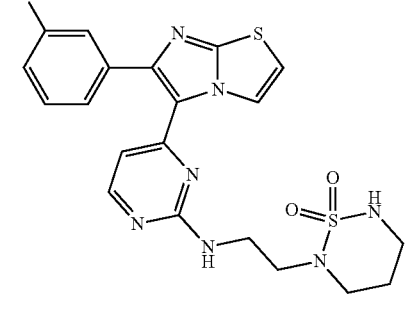 14II | 0.72 |
| 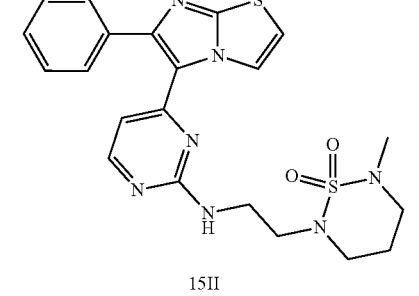 15II | 0.47 |
| 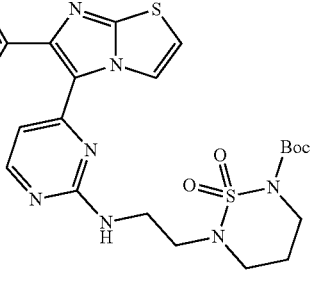 PL | 0.47 |

As shown in Table 3, most of the compounds 2II, 9II, 10II, and 12II to 15II of the present disclosure were found to have excellent proliferation-inhibitory effects, as compared with the known imidazothiazole-based compounds P1 to P5. Particularly, when similar structures were compared with each other (compounds P1/9II, P2/10II, P3/2II, and P4/12II), it was more clearly found that the compounds of the present disclosure have more remarkable effects.

<Experimental Example 2> Measurement of Protein Kinase Enzymatic Activity

Whether the imidazooxazole- and imidazothiazole-based compounds of the present disclosure inhibit kinase enzymatic activity involved with inhibitory activities against melanoma cell line proliferation was examined by the following method.

Reaction biology kinase hotspot service (http://www.reactionbiology.com) was used to measure $IC_{50}$. In a final reaction volume of 25 μL, kinase (5 mU to 10 mU) was incubated with 25 mM Tris (pH 7.5), 0.02 mM EGTA, 0.66 mg/ml of myelin basic protein, 10 mM magnesium acetate, and [$^{33}$P-ATP] (specific activity of about 500 CPM/pmol, concentration as required). The reaction was initiated by addition of Mg-ATP mix. After incubation for 40 min at room temperature, the reaction was stopped by addition of 5 μl of a 3% phosphoric acid solution. 10 μL of the reaction was then spotted onto a P30 filtermat and washed three times for 5 minutes in 75 mM phosphoric acid and once in methanol prior to drying and scintillation counting.

TABLE 4

Inhibitory effects against kinase activities of B-RAF, V600E-RAF, and C-RAF (nM)

|        | B-RAF | V600E-B-RAF | C-RAF |
|--------|-------|-------------|-------|
| 1II    | 3.23  | 1.85        | 2.95  |
| 2II    | <0.04 | 0.67        | 0.75  |
| 2III   | 459   | 77          | ND    |
| 8III   | 687   | 98          | ND    |
| 25III  | 5.70  | 1.00        | ND    |
| 31II   | 4.19  | 0.98        | 7.83  |
| GW5074 | 8.52  | 2.96        | 2.58  |
| Vemurafenib | 100 | 31       | 48    |

As shown in Table 4, among the compounds according to the present disclosure, the compounds 1II, 2II, 25III, and 31III showed excellent inhibitory effects against enzymatic activities of B-RAF, V600E-RAF, and C-RAF, which were higher than those of GW5074 and vemurafenib.

Taken together, the compounds according to the present disclosure showed excellent inhibitory effects against protein kinases, in particular, many different protein kinases, for example, V600E RAF, B-RAF, C-RAF, MAPK14, FLT3, and GSK3P3, each causing diseases associated with abnormal cell growth such as tumor cells, and thus the compounds may be usefully applied to prevention and treatment of tumor cell growth.

<Experimental Example 3> Tumor-Inhibitory Effects in Melanoma Mouse Model

To examine whether the inhibitory effects against proliferation of melanoma cells and the inhibitory effects against enzymatic activities of B-RAF, V600E-RAF, and C-RAF observed at the cell level are also reproduced in animal models, the following experiment was performed.

In this experiment, A375P cell line which is a human-derived malignant melanoma cell line was subcutaneously administered to nude mice to prepare xenograft models, and the test material (compound 2II) was administered to the xenograft models to evaluate anti-cancer effects (GI: an excipient control group, G2: a group administered with 20 mg/kg/day of the test material, and G3: a group administered with 50 mg/kg/day of the test material).

Results are shown in FIG. 1 and Table 5 below.

TABLE 5

Increase of tumor size in melanoma xenograft models (compound 2II)

| | Group (mg/kg/day) | | |
|---|---|---|---|
| Day | G1 (0) | G2 (20 mg/kg/day) | G3 (50 mg/kg/day) |
| 0  | 148.94 ± 6.23   | 145.08 ± 20.85  | 149.36 ± 20.91 |
| 4  | 271.05 ± 85.51  | 271.88 ± 60.05  | 276.08 ± 86.17 |
| 7  | 552.89 ± 311.28 | 556.42 ± 161.21 | 442.88 ± 73.08 |
| 11 | 984.73 ± 589.89 | 978.91 ± 258.24 | 754.16 ± 211.86 |
| 14 | 1697.7 ± 931.04 | 1711.5 ± 631.79 | 1174.7 ± 411.22 |
| 18 | 2512.6 ± 1491.9 | 2438.5 ± 962.99 | 1543.9 ± 411.21 |
| 21 | 3557.1 ± 2162.2 | 3200.6 ± 944.99 | 2063.1 ± 657.93 |

General symptoms were examined, and as a result, no deaths or no abnormalities in general symptoms were observed. Body weights were examined, and as a result, the body weight of the group (G3) administered with 50 mg/kg/day of the test material was significantly low at 14 days and 21 days after administration of the test material, as compared with that of the control group (G1), and the body weight gain of the group administered with 50 mg/kg/day of the test material was also significantly low, as compared with that of the excipient control group.

Tumor sizes were measured, and as a result, there was no significant difference between all experimental groups, but it was observed that increase of the tumor size was inhibited in a dose-dependent manner in the groups administered with the test material.

In conclusion, when intravenous administration of the test material to the malignant melanoma xenograft models prepared using nude mice was repeated twice per week for 3 weeks, increase of the tumor size was found to be inhibited in a dose-dependent manner, although the body weight of the test material-administered group was significantly low or tend to decrease and reduction in the body weight gain thereof was observed, as compared with that of the control group. Accordingly, it was confirmed that the compounds of the present disclosure show inhibitory activity against tumor growth in the animal test as well as at the cell level, suggesting that the compounds may have therapeutic and prophylactic effects on tumors.

The invention claimed is:

1. A compound represented by the following Chemical Formula S or a solvate, stereoisomer, or pharmaceutically acceptable salt thereof:

Chemical Formula S

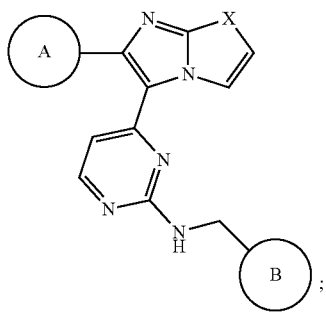

wherein:
A is

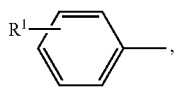

wherein,
when X is O, $R^1$ is hydrogen, halogen, $C_1$-$C_4$ alkoxy, or hydroxyl, and
when X is S, $R^1$ is hydrogen, Cl, Br, I, $C_1$-$C_4$ alkoxy, or hydroxyl, and
B is

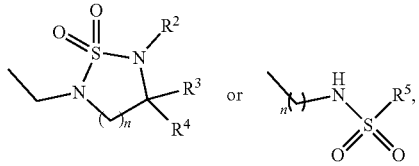

wherein,
n 1 or 2,
$R^2$, $R^3$, and $R^4$ are each independently hydrogen, tert-butyloxycarbonyl, or $C_1$-$C_4$ linear or branched alkyl, $C_5$-$C_{12}$ aryl, $C_5$-$C_{12}$ heteroaryl, or $C_5$-$C_{12}$ heterocycloalkyl unsubstituted or substituted with one or more substituents, and
$R^5$ is M or M-Y, wherein M and Y are each independently $C_5$-$C_{12}$ aryl, $C_5$-$C_{12}$ heteroaryl, $C_5$-$C_{12}$ aryl, $C_1$-$C_4$ alkyl, $C_5$-$C_{12}$ heteroaryl, $C_1$-$C_4$ alkyl, $C_5$-$C_{12}$ cycloalkyl, or $C_5$-$C_{12}$ heterocycloalkyl unsubstituted or substituted with one or more substituents,
wherein the one or more substituents are selected from the group consisting of halogen, $C_1$-$C_4$ linear or branched alkyl, $C_1$-$C_4$ alkoxy, trifluoromethyl, hydroxyl, amine, $C_1$-$C_4$ alkylamine, nitro, amide, $C_1$-$C_4$ alkylamide, urea, and acetyl.

2. The compound or the solvate, stereoisomer, or pharmaceutically acceptable salt thereof of claim 1, wherein,
when X is O, $R^1$ is hydrogen, fluoro, methoxy, or hydroxyl,
$R^2$, $R^3$, and $R^4$ are each independently hydrogen, tert-butyloxycarbonyl, ethyl, methyl, or benzyl, and
$R^5$ is phenyl unsubstituted or substituted with one or more substituents, wherein the one or more substituents being selected from the group consisting of methyl, ethyl, fluoro, trifluoromethyl, hydroxyl, methoxy, nitro, amide, urea, and acetyl.

3. The compound or the solvate, stereoisomer, or pharmaceutically acceptable salt thereof of claim 1, wherein the Chemical Formula S is a compound represented by any one of the following Chemical Formulae I to IV:

I

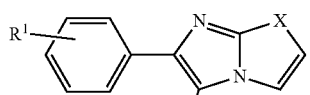
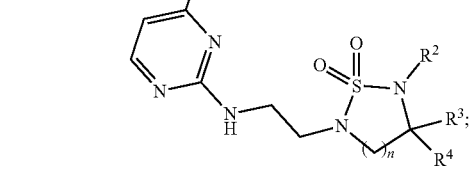

II

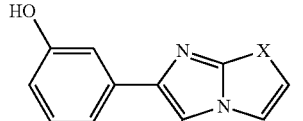
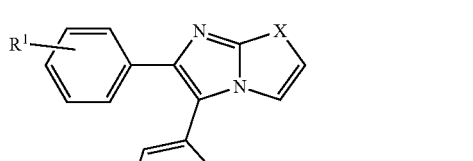

III

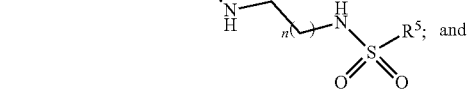
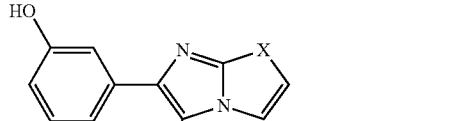

IV

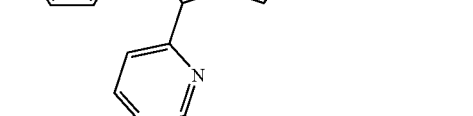
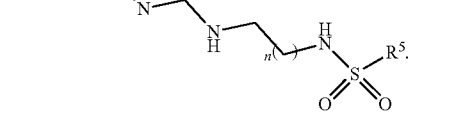

4. The compound or the solvate, stereoisomer, or pharmaceutically acceptable salt thereof of claim 1, wherein the compound represented by Chemical Formula S is selected from the group consisting of:
2-(2-((4-(6-(4-fluorophenyl)imidazo[2,1-b]oxazol-5-yl)pyrimidin-2-yl)amino)ethyl)-5-methyl-1,2,5-thiadiazolidine 1,1-dioxide;
2-ethyl-5-(2-((4-(6-(4-fluorophenyl)imidazo[2,1-b]oxazol-5-yl)pyrimidin-2-yl)amino)ethyl)-1,2,5-thiadiazolidine 1,1-dioxide;

2-benzyl-5-(2-((4-(6-(4-fluorophenyl)imidazo[2,1-b]ox-azol-5-yl)pyrimidin-2-yl)amino)ethyl)-1,2,5-thiadiazolidine 1,1-dioxide;
2-(2-((4-(6-(3-methoxyphenyl)imidazo[2,1-b]oxazol-5-yl)pyrimidin-2-yl)amino)ethyl)-5-methyl-1,2,5-thiadiazolidine 1,1-dioxide;
2-ethyl-5-(2-((4-(6-(3-methoxyphenyl)imidazo[2,1-b]oxazol-5-yl)pyrimidin-2-yl)amino)ethyl)-1,2,5-thiadiazolidine 1,1-dioxide;
2-benzyl-5-(2-((4-(6-(3-methoxyphenyl)imidazo[2,1-b]oxazol-5-yl)pyrimidin-2-yl)amino)ethyl)-1,2,5-thiadiazolidine 1,1-dioxide;
2-(2-((4-(6-(3-methoxyphenyl)imidazo[2,1-b]oxazol-5-yl)pyrimidin-2-yl)amino)ethyl)-1,2,5-thiadiazolidine 1,1-dioxide;
2-(2-((4-(6-(3-methoxyphenyl)imidazo[2,1-b]oxazol-5-yl)pyrimidin-2-yl)amino)ethyl)-4,4-dimethyl-1,2,5-thiadiazolidine 1,1-dioxide;
2-(2-((4-(6-(3-methoxyphenyl)imidazo[2,1-b]oxazol-5-yl)pyrimidin-2-yl)amino)ethyl)-6-methyl-1,2,6-thiadiazinane 1,1-dioxide;
2-(2-((4-(6-(3-methoxyphenyl)imidazo[2,1-b]oxazol-5-yl)pyrimidin-2-yl)amino)ethyl)-1,2,6-thiadiazinane 1,1-dioxide;
2-(2-((4-(6-(3-hydroxylphenyl)imidazo[2,1-b]oxazol-5-yl)pyrimidin-2-yl)amino)ethyl)-5-methyl-1,2,5-thiadiazolidine 1,1-dioxide;
2-ethyl-5-(2-((4-(6-(3-hydroxylphenyl)imidazo[2,1-b]oxazol-5-yl)pyrimidin-2-yl)amino)ethyl)-1,2,5-thiadiazolidine 1,1-dioxide;
2-benzyl-5-(2-((4-(6-(3-hydroxylphenyl)imidazo[2,1-b]oxazol-5-yl)pyrimidin-2-yl)amino)ethyl)-1,2,5-thiadiazolidine 1,1-dioxide;
2-(2-((4-(6-(3-hydroxylphenyl)imidazo[2,1-b]oxazol-5-yl)pyrimidin-2-yl)amino)ethyl)-1,2,5-thiadiazolidine 1,1-dioxide;
2-(2-((4-(6-(3-hydroxylphenyl)imidazo[2,1-b]oxazol-5-yl)pyrimidin-2-yl)amino)ethyl)-4,4-dimethyl-1,2,5-thiadiazolidine 1,1-dioxide;
2-(2-((4-(6-(3-hydroxylphenyl)imidazo[2,1-b]oxazol-5-yl)pyrimidin-2-yl)amino)ethyl)-6-methyl-1,2,6-thiadiazinane 1,1-dioxide;
tert-butyl-6-(2-((4-(6-(3-hydroxylphenyl)imidazo[2,1-b]oxazol-5-yl)pyrimidin-2-yl)amino)ethyl)-1,2,6-thiadiazinane-2-carboxylate 1,1-dioxide;
2-(2-((4-(6-(3-hydroxylphenyl)imidazo[2,1-b]oxazol-5-yl)pyrimidin-2-yl)amino)ethyl)-1,2,6-thiadiazinane 1,1-dioxide;
4-fluoro-N-(2-((4-(6-phenylimidazo[2,1-b]thiazol-5-yl)pyrimidin-2-yl)amino)ethyl)benzenesulfonamide;
4-methoxy-N-(2-((4-(6-phenylimidazo[2,1-b]thiazol-5-yl)pyrimidin-2-yl)amino)ethyl)benzenesulfonamide;
4-methyl-N-(2-((4-(6-phenylimidazo[2,1-b]thiazol-5-yl)pyrimidin-2-yl)amino)ethyl)benzenesulfonamide;
N-(2-((4-(6-(4-fluorophenyl)imidazo[2,1-b]oxazol-5-yl)pyrimidin-2-yl)amino)ethyl)benzenesulfonamide;
3-fluoro-N-(2-((4-(6-(4-fluorophenyl)imidazo[2,1-b]oxazol-5-yl)pyrimidin-2-yl)amino)ethyl)benzenesulfonamide;
4-fluoro-N-(2-((4-(6-(4-fluorophenyl)imidazo[2,1-b]oxazol-5-yl)pyrimidin-2-yl)amino)ethyl)benzenesulfonamide;
N-(2-((4-(6-(4-fluorophenyl)imidazo[2,1-b]oxazol-5-yl)pyrimidin-2-yl)amino)ethyl)-4-iodobenzenesulfonamide;
N-(2-((4-(6-(4-fluorophenyl)imidazo[2,1-b]oxazol-5-yl)pyrimidin-2-yl)amino)ethyl)-4-methoxybenzenesulfonamide;
N-(2-((4-(6-(4-fluorophenyl)imidazo[2,1-b]oxazol-5-yl)pyrimidin-2-yl)amino)ethyl)-4-methyl benzenesulfonamide;
N-(2-((4-(6-(4-fluorophenyl)imidazo[2,1-b]oxazol-5-yl)pyrimidin-2-yl)amino)ethyl)-4-(trifluoromethyl)benzenesulfonamide;
N-(2-((4-(6-(4-fluorophenyl)imidazo[2,1-b]oxazol-5-yl)pyrimidin-2-yl)amino)ethyl)-3,4-dimethoxybenzenesulfonamide;
N-(2-((4-(6-(4-fluorophenyl)imidazo[2,1-b]oxazol-5-yl)pyrimidin-2-yl)amino)ethyl)-3,4-dimethylbenzenesulfonamide;
N-(2-((4-(6-(4-fluorophenyl)imidazo[2,1-b]oxazol-5-yl)pyrimidin-2-yl)amino)ethyl)naphthalene-2-sulfonamide;
N-(2-((4-(6-(3-methoxyphenyl)imidazo[2,1-b]thiazol-5-yl)pyrimidin-2-yl) amino)ethyl)benzenesulfonamide;
4-fluoro-N-(2-((4-(6-(3-methoxyphenyl)imidazo[2,1-b]thiazol-5-yl)pyrimidin-2-yl)amino)ethyl)benzenesulfonamide;
4-methoxy-N-(2-((4-(6-(3-methoxyphenyl)imidazo[2,1-b]thiazol-5-yl)pyrimidin-2-yl)amino)ethyl)benzenesulfonamide;
N-(2-((4-(6-(3-methoxyphenyl)imidazo[2,1-b]thiazol-5-yl)pyrimidin-2-yl)amino)ethyl)-4-methylbenzenesulfonamide;
N-(2-((4-(6-(3-methoxyphenyl)imidazo[2,1-b]thiazol-5-yl)pyrimidin-2-yl)amino)ethyl)-4-(trifluoromethyl)benzenesulfonamide;
3-fluoro-N-(2-((4-(6-(3-methoxyphenyl)imidazo[2,1-b]thiazol-5-yl)pyrimidin-2-yl)amino)ethyl)benzenesulfonamide;
N-(2-((4-(6-(3-methoxyphenyl)imidazo[2,1-b]thiazol-5-yl)pyrimidin-2-yl)amino)ethyl)naphthalene-2-sulfonamide;
4-fluoro-N-(2-((4-(6-(4-methoxyphenyl)imidazo[2,1-b]thiazol-5-yl)pyrimidin-2-yl)amino)ethyl)benzenesulfonamide;
4-methoxy-N-(2-((4-(6-(4-methoxyphenyl)imidazo[2,1b]thiazol-5-yl)pyrimidin-2-yl)amino)ethyl)benzenesulfonamide;
N-(2-((4-(6-(4-methoxyphenyl)imidazo[2,1-b]thiazol-5-yl)pyrimidin-2-yl)amino)ethyl)-4-methylbenzenesulfonamide;
N-(2-((4-(6-(4-methoxyphenyl)imidazo[2,1-b]thiazol-5-yl)pyrimidin-2-yl)amino)ethyl)naphthalene-2-sulfonamide;
4-fluoro-N-(3-((4-(6-phenylimidazo[2,1-b]thiazol-5-yl)pyrimidin-2-yl)amino)propyl)benzenesulfonamide;
4-methoxy-N-(3-((4-(6-phenylimidazo[2,1-b]thiazol-5-yl)pyrimidin-2-yl)amino)propyl)benzenesulfonamide;
4-methyl-N-(3-((4-(6-phenylimidazo[2,1-b]thiazol-5-yl)pyrimidin-2-yl)amino)propyl)benzenesulfonamide;
N-(3-((4-(6-(4-fluorophenyl)imidazo[2,1-b]oxazol-5-yl)pyrimidin-2-yl)amino)propyl)benzenesulfonamide;
4-fluoro-N-(3-((4-(6-(4-fluorophenyl)imidazo[2,1-b]oxazol-5-yl)pyrimidin-2-yl)amino)propyl)benzenesulfonamide;
N-(3-((4-(6-(4-fluorophenyl)imidazo[2,1-b]oxazol-5-yl)pyrimidin-2-yl)amino)propyl)-4-iodobenzenesulfonamide;
N-(3-((4-(6-(4-fluorophenyl)imidazo[2,1-b]oxazol-5-yl)pyrimidin-2-yl)amino)propyl)-4-methoxybenzenesulfonamide;

N-(3-((4-(6-(4-fluorophenyl)imidazo[2,1-b]oxazol-5-yl)pyrimidin-2-yl)amino)propyl)-4-methylbenzenesulfonamide;
N-(3-((4-(6-(4-fluorophenyl)imidazo[2,1-b]oxazol-5-yl)pyrimidin-2-yl)amino)propyl)-4-(trifluoromethyl)benzenesulfonamide;
3-fluoro-N-(3-((4-(6-(4-fluorophenyl)imidazo[2,1-b]oxazol-5-yl)pyrimidin-2-yl)amino)propyl)benzenesulfonamide;
N-(3-((4-(6-(4-fluorophenyl)imidazo[2,1-b]oxazol-5-yl)pyrimidin-2-yl)amino)propyl)-3,4-dimethoxybenzenesulfonamide;
N-(3-((4-(6-(4-fluorophenyl)imidazo[2,1-b]oxazol-5-yl)pyrimidin-2-yl)amino)propyl)-3,4-dimethylbenzenesulfonamide;
N-(3-((4-(6-(4-fluorophenyl)imidazo[2,1-b]oxazol-5-yl)pyrimidin-2-yl)amino)propyl)naphthalene-2-sulfonamide;
N-(3-((4-(6-(3-methoxyphenyl)imidazo[2,1-b]thiazol-5-yl) pyrimidin-2-yl)amino)propyl)benzenesulfonamide;
3-fluoro-N-(3-((4-(6-(3-methoxyphenyl)imidazo[2,1-b]thiazol-5-yl)pyrimidin-2-yl)amino)propyl)benzenesulfonamide;
4-fluoro-N-(3-((4-(6-(3-methoxyphenyl)imidazo[2,1-b]thiazol-5-yl)pyrimidin-2-yl)amino)propyl)benzenesulfonamide;
4-methoxy-N-(3-((4-(6-(3-methoxyphenyl)imidazo[2,1-b]thiazol-5-yl)pyrimidin-2-yl)amino)propyl)benzenesulfonamide;
N-(3-((4-(6-(3-methoxyphenyl)imidazo[2,1-b]thiazol-5-yl)pyrimidin-2-yl)amino)propyl)-4-methylbenzenesulfonamide;
N-(3-((4-(6-(3-methoxyphenyl)imidazo[2,1-b]thiazol-5-yl)pyrimidin-2-yl)amino)propyl)naphthalene-2-sulfonamide;
4-hydroxyl-N-(2-((4-(6-phenylimidazo[2,1-b]thiazol-5-yl)pyrimidin-2-yl)amino)ethyl)benzenesulfonamide;
N-(2-((4-(6-(4-fluorophenyl)imidazo[2,1-b]oxazol-5-yl)pyrimidin-2-yl)amino)ethyl)-4-hydroxylbenzenesulfonamide;
4-fluoro-N-(2-((4-(6-(3-hydroxylphenyl)imidazo[2,1-b]thiazol-5-yl)pyrimidin-2-yl)amino)ethyl)benzenesulfonamide;
4-hydroxyl-N-(2-((4-(6-(3-hydroxylphenyl)imidazo[2,1-b]thiazol-5-yl)pyrimidin-2-yl)amino)ethyl)benzenesulfonamide;
N-(2-((4-(6-(3-hydroxylphenyl)imidazo[2,1-b]thiazol-5-yl)pyrimidin-2-yl)amino)ethyl)-4-methylbenzenesulfonamide;
4-hydroxyl-N-(2-((4-(6-(4-hydroxylphenyl)imidazo[2,1-b]thiazol-5-yl)pyrimidin-2-yl)amino)ethyl)benzenesulfonamide;
N-(2-((4-(6-(4-hydroxylphenyl)imidazo[2,1-b]thiazol-5-yl)pyrimidin-2-yl)amino)ethylbenzenesulfonamide;
N-(3-((4-(6-(4-fluorophenyl)imidazo[2,1-b]oxazol-5-yl)pyrimidin-2-yl)amino)propyl)-4-hydroxylbenzenesulfonamide;
N-(3-((4-(6-(3-hydroxylphenyl)imidazo[2,1-b]thiazol-5-yl)pyrimidin-2-yl)amino)propyl)benzenesulfonamide; and
4-fluoro-N-(3-((4-(6-(3-hydroxylphenyl)imidazo[2,1-b]thiazol-5-yl)pyrimidin-2-yl)amino)propyl)benzenesulfonamide.

5. A method of preparing the compound or the solvate, stereoisomer, or pharmaceutically acceptable salt thereof of claim 1, the method comprising:

cyclizing a compound of Chemical Formula 1 and a compound of Chemical Formula 2 to prepare a compound of Chemical Formula 3;
reacting the compound of Chemical Formula 3 with 4-chloro-2-(methylthio)pyrimidine to prepare a compound of Chemical Formula 4;
oxidizing the compound of Chemical Formula 4 to prepare a compound of Chemical Formula 5; and
reacting the compound of Chemical Formula 5 with an N-aminoethylcyclic sulfonamide derivative or an N-(2-aminoethyl)benzenesulfonamide derivative in the presence of a base to prepare the compound of Chemical Formula S:

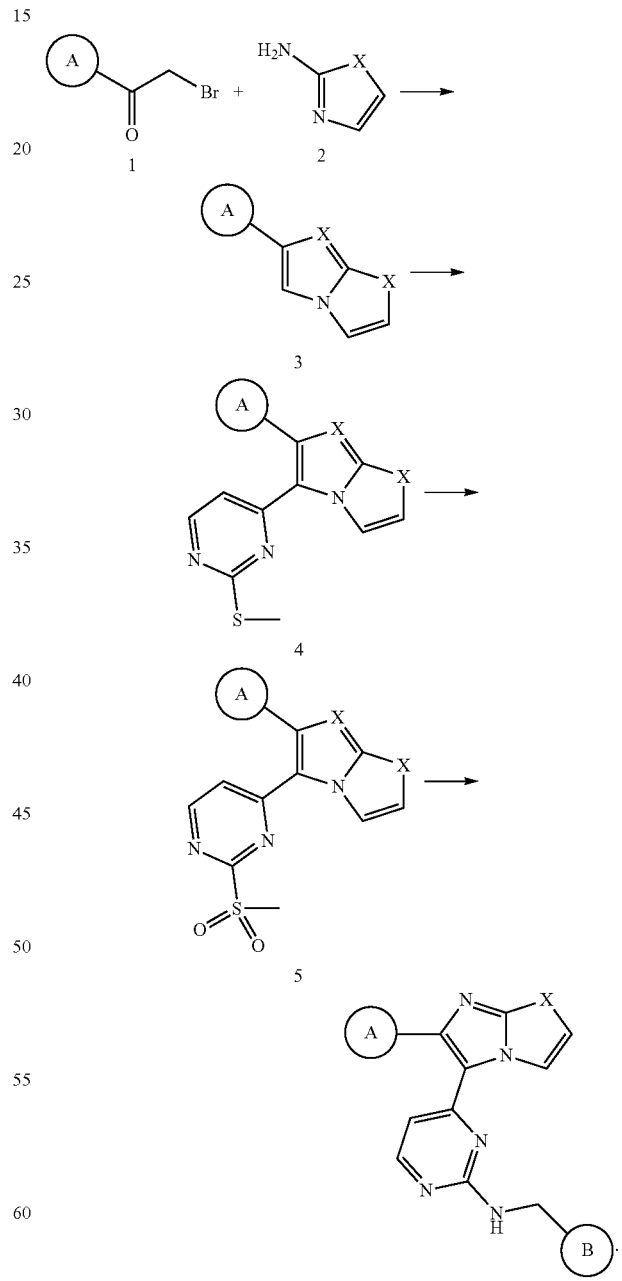

Chemical Formula S

6. A pharmaceutical composition for preventing and treating a tumor, the pharmaceutical composition comprising the compound or the solvate, stereoisomer, or pharmaceutically acceptable salt thereof of claim 1 as an active ingredient.

7. The pharmaceutical composition of claim 6, wherein the compound or the solvate, stereoisomer, or pharmaceutically acceptable salt thereof inhibits protein kinase to inhibit proliferation of tumor cells.

8. The pharmaceutical composition of claim 7, wherein the protein kinase is selected from the group consisting of V600E RAF, B-RAF, C-RAF, mitogen-activated protein kinase 14 (MAPK14), Fms-like tyrosine kinase 3 (FLT3), and glycogen synthase kinase 3 beta (GSK313).

9. The pharmaceutical composition of claim 6, wherein the tumor is selected from the group consisting of lung cancer, liver cancer, esophageal cancer, stomach cancer, colorectal cancer, small intestine cancer, pancreatic cancer, melanoma, breast cancer, oral cancer, brain tumor, thyroid cancer, parathyroid cancer, renal cancer, cervical cancer, sarcoma, prostate cancer, urethral cancer, bladder cancer, testicular cancer, hematological malignancy, lymphoma, skin cancer, psoriasis, and fibroadenoma.

10. A method of preventing or treating a tumor, the method comprising administering the pharmaceutical composition of claim 6 to a subject having or at risk of developing a tumor.

* * * * *